United States Patent
Shen et al.

(10) Patent No.: US 8,476,485 B2
(45) Date of Patent: Jul. 2, 2013

(54) NON-HUMAN ANIMAL MODEL FOR AMYOTROPHIC LATERAL SCLEROSIS (ALS) WITH LOSS-OF-TDP-43 FUNCTION

(75) Inventors: Che-Kun James Shen, Taipei (TW); Lien-Szu Wu, Tainan (TW)

(73) Assignee: Academia Sinica, Taipei (TW)

( * ) Notice: Subject to any disclaimer, the term of this patent is extended or adjusted under 35 U.S.C. 154(b) by 203 days.

(21) Appl. No.: 13/166,147

(22) Filed: Jun. 22, 2011

(65) Prior Publication Data
US 2011/0321179 A1 Dec. 29, 2011

Related U.S. Application Data

(60) Provisional application No. 61/357,996, filed on Jun. 24, 2010.

(51) Int. Cl.
*A01K 67/027* (2006.01)
*G01N 33/00* (2006.01)

(52) U.S. Cl.
USPC ..................................... 800/18; 800/9; 800/3

(58) Field of Classification Search
USPC ................................... 800/18, 9, 3
See application file for complete search history.

(56) References Cited

PUBLICATIONS

Clark et al. (2003) Nature Reviews: Genetics. vol. 4, 825-833.*
Niemann et al (2005) Rev. Sci, Tech. Off. Int. Spiz. vol. (24), 285-298.*
Wheeler (2001) Theriogenology. vol. 56, 1345-1369.*
Prelle et al. (2002) Anat. Histol. Embryol., vol. 31, 169-186.*
Doetschmann (1999) Lab. Animal Sci., vol. 49 (2), 137-143.*
Moens et al. (1993) Development, vol. 199, 485-499.*
Jacks et al. (1992) Nature, vol. 359, 295-300.*
Kuehn et al. (1987) Nature, vol. 326, 295-298.*
Jaenisch (1988) Science, vol. 240, 1468-1474.*
Bento-Abreu et al. (2010) J. Neurosci., vol. 31, 2247-2265.*
Kreamer et al. (2010) Acta Neuropathol., vol. 119, 409-419.*
Wils et al. (2010) PNAS, vol. 107(8), 3858-3863.*
Watanabe et al. (2001) "Histological Evidence of Protein Aggregation in Mutant SOD1 Transgenic Mice and in Amyotrophic Lateral Sclerosis Neural Tissues" Neurobiology of Disease 8,933-941.
Kraemer BC et al. ("Loss of murine TDP-43 disrupts motor function and plays an essential role in embryogenesis" (2010) Acta Neuropathol 119(4):409-19).
Wu LS et al ("TDP-43, a neuro-pathosignature facor: is essential for early mouse embryogenesis" Genesis (2010)48 (1):56-62).
Li XM et al. ("Retrograde regulation of motoneuron differentiation by muscle beta-catenin" (2008) Nat Neurosci 11 (3):262-8).
T. F. Gendron et al. ("Transactive response DNA-binding protein 43 (TDP-43): mechanisms of neurodegeneration" (2010) Neuropathology and Applied Neurobiology36, 97-112).
André Bento-Abreu et al. ("The neurobiology of amyotrophic lateral sclerosis" (2010) European Journal of Neuroscience 31 (12):2247-2265).

* cited by examiner

*Primary Examiner* — Anne Marie S Wehbe
(74) *Attorney, Agent, or Firm* — Hsiu-Ming Saunders; Intellectual Property Connections, Inc.

(57) ABSTRACT

A non-human animal model for amyotrophic lateral sclerosis (ALS) is disclosed. The animal model comprises a rodent whose spinal cord motor neurons have a loss of TAR-DNA binding protein-43 (TDP-43) function and phenotypes exhibit ALS-like symptoms. A method for identifying a candidate agent for treating, preventing and/or inhibiting ALS associated with a loss-of-function of TDP-43 is also disclosed.

20 Claims, 9 Drawing Sheets

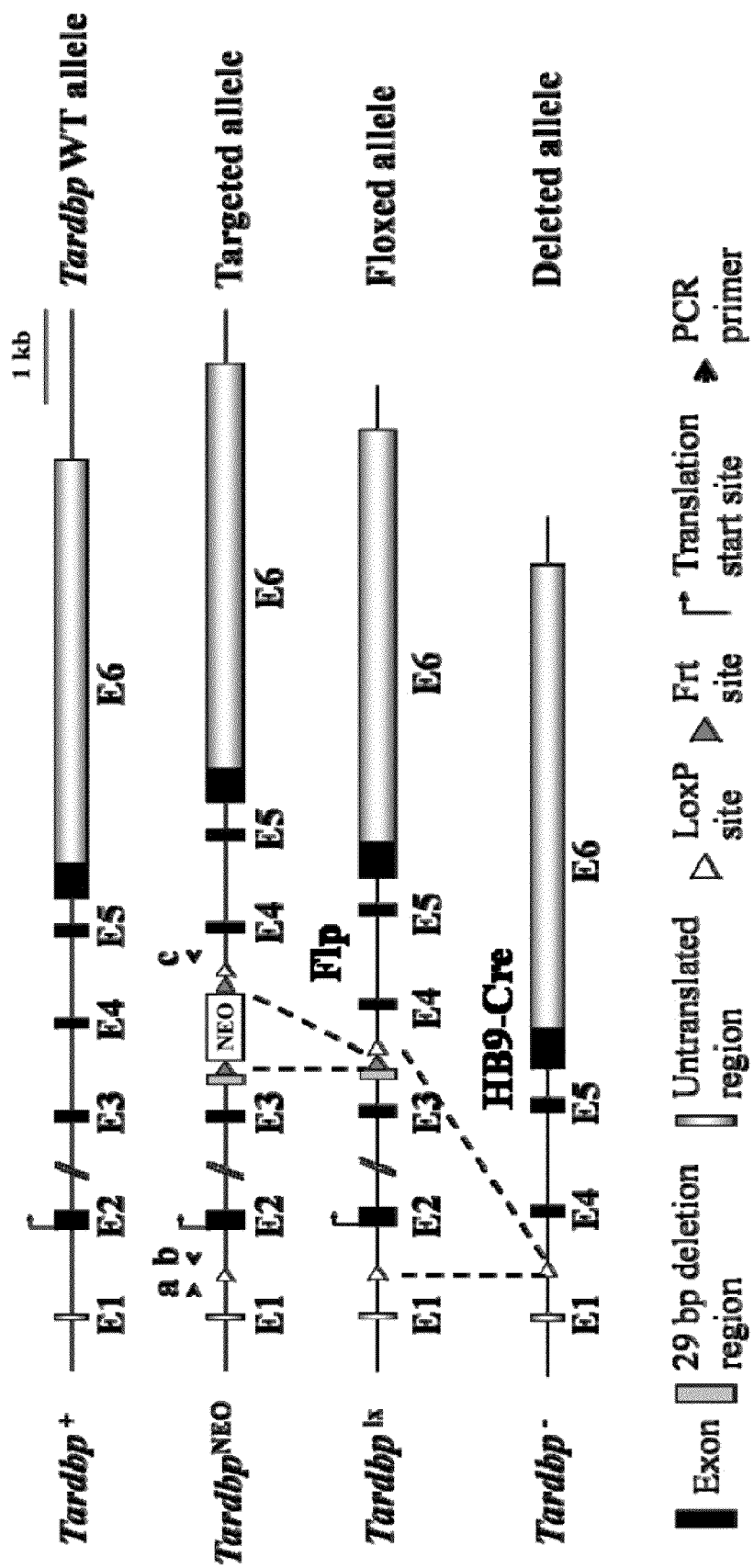

*Tardbp*<sup>lx/−</sup>        HB9–*Tardbp*<sup>lx/−</sup>

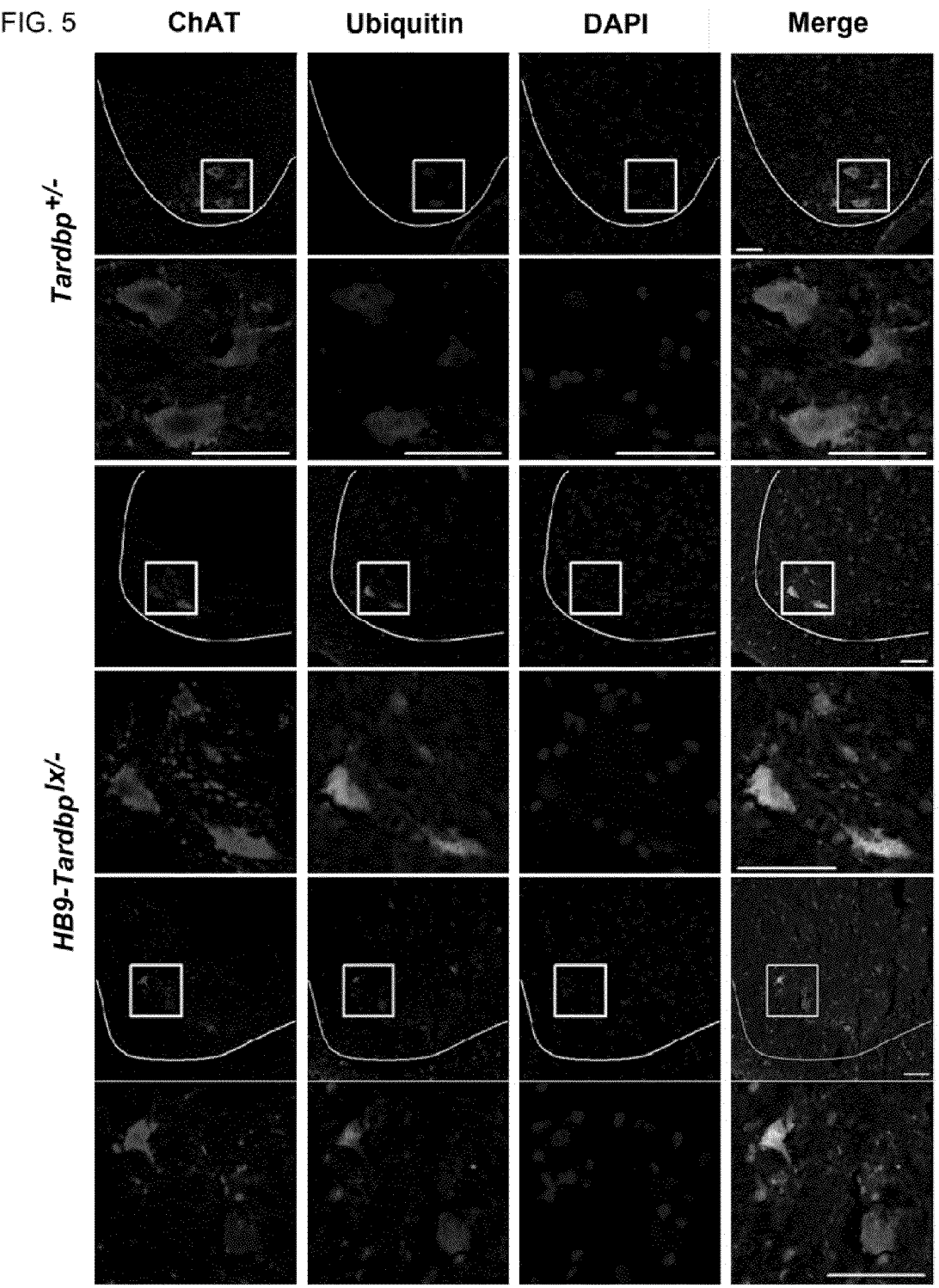

NON-HUMAN ANIMAL MODEL FOR AMYOTROPHIC LATERAL SCLEROSIS (ALS) WITH LOSS-OF-TDP-43 FUNCTION

REFERENCE TO RELATED APPLICATION

The present application claims the priority to U.S. Provisional Application Ser. No. 61/357,996, filed Jun. 24, 2010, which is herein incorporated by reference in its entirety.

FIELD OF THE INVENTION

The present invention relates to the field of amyotrophic lateral sclerosis (ALS).

BACKGROUND OF THE INVENTION

Amyotrophic lateral sclerosis (ALS; also known as Lou Gehrig's disease and motor neuron disease) is a progressive, fatal, adult-onset degenerative disorder of motor neurons in the primary motor cortex, corticospinal tracts, brainstem and spinal cord, leading to paralysis of voluntary muscles. Currently, the incidence and prevalence of ALS are 1-2 per 100,000 each year, respectively, with a lifetime ALS risk of 1 in 400 to 1 in 1,000. Most incidences of ALS are sporadic but approximately 10% of patients have a familial history (known as familial ALS; fALS). In both sALS and fALS, there are progressive manifestations of dysfunction of the lower motor neurons and cortical motor neurons but without sensory symptoms. Age and gender are documented sALS risk factors with a male-to-female ratio of 3:2 among the patients. Among the mutations associated with ALS, those in the Copper-Zinc superoxide dismutase (SOD1) gene have long been thought to cause the ALS disease through a toxic gain of function rather than impairment of the antioxidant function of the SOD1 enzyme. Other genes with mutations associated with the fALS include alsin (ALS2), senataxin (ALS4), vesicle associated membrane protein (VAPB, ALS8), Angiogenin and the p150 subunit of dynactin (DCTN1). Recently, more than thirty mutations in the TDP-43-coding region of Tardbp have been identified in ALS patients with or without apparent family history, corresponding to approximately 4% of fALS and less than 1% of sALS. Most patients with TDP-43 mutation(s) develop a classical ALS phenotype without cognitive deficit suggesting an important role of TDP-43 in the development of ALS.

TDP-43, or TAR DNA-binding protein-43, is a ubiquitously expressed nuclear protein encoded by one of the mRNA isoforms from the highly conserved Tardbp gene. It is a RNA-binding protein involved in transcriptional repression, pre-mRNA splicing, and translation. TDP-43 has also been identified as the major pathological signature protein of intracellular inclusions typical for disease cells of a range of neurodegenerative diseases, including frontotemporal lobar degeneration with ubiquitin-positive, tau- and α-synuclein-negative inclusions (FTLD-U) and amyotrophic lateral sclerosis (ALS). The TDP-43 molecules in the diseased cells of the patients' brains or spinal cords are characterized by abnormal ubiquitination, hyperphosphorylation and partial cleavage to generate ~25 kDa and 35 kDa C-terminal fragment(s). Furthermore, TDP-43 is partially or completely cleared from the nuclei of either neuronal or glial cells containing the TDP-43 (+) and ubiquitin (+) aggregates/inclusions, or UBIs, in the cytoplasm.

Several mouse models have been established for ALS disease, which include strains of rodents that are transgenic with SOD1, ALS2-knockout mice, and mice with genetically engineered genes coding for the neurofilament subunits. Among these, the human mutant SOD1 (mSOD1) transgenic mouse model is currently the most widely used one because it shares several clinical phenotypes with ALS patients. The first symptom of mSOD1 mice is a fine "jittering/tremor" in one or more of the limbs, which appears at approximately 90 to 100 days of age. At later stages, the mice begin a clinical course, first with muscle weakness and/or paresis in the hind limbs, followed by ascent of paresis to the forelimbs and finally severe quadriplegia. The cytopathological features of the mSOD1 Tg mice include motor neuron loss with astrocytosis, the presence of SOD1-positive inclusions including Lewy body-like hyaline inclusions/astrocyte hyline inclusions, and vacuole formation. Among these three pathologic features, motor neuron loss with gliosis is the most essential one shared between the mSOD1 Tg mice and ALS.

Overexpression of TDP-43 in transgenic rodents could also lead to development of motor neuron disease-like symptoms. These Tg rodents develop one or more of several symptoms, which include motor neuron dysfunction, muscle defect-related pathology such as spastic paralysis, and neuronal loss. The life spans of some of these Tg mouse lines are short, likely due to the relatively low motor-neuron specificity of the promoters used, e.g., Thy1, prion, etc. Finally, the appearance of cells with cytoplasmic TDP-43(+) UBIs and TDP-43 depleted nuclei at later stages of pathogenesis of the TDP-43 Tg mice suggest that the disease phenotypes in the TDP-43 Tg mice may result in part from loss-of-function of TDP-43. However, the pathological phenotypes of the mice could also be caused entirely by gain-of-toxicity from overexpression of the exogenous TDP-43. Thus, the relative contributions of loss-of-function and gain-of-cytotoxicity to the neurodegeneration in FTLD-U and ALS with TDP-43 (+) UBIs are not clear. In addition, regardless of its currently known biochemical and structural properties, the physiological functions of TDP-43 in different mammalian tissues are also unknown.

A previously unaddressed need exists in the art to address the aforementioned deficiencies and inadequacies, especially in connection with the roles of TDP-43 in ALS.

SUMMARY OF THE INVENTION

In one aspect, the invention relates to a non-human animal model for amyotrophic lateral sclerosis (ALS), in which the animal model comprises a rodent whose spinal cord motor neurons have a loss of TAR-DNA binding protein-43 (TDP-43) function and the rodent exhibits ALS-like symptoms.

In another aspect, the invention relates to a tissue or a motor neuron which is isolated from the spinal cord of the animal model as aforementioned.

Further in another aspect, the invention relates to a method for identifying an agent with potential for treatment of a disease associated with a loss of TAR-DNA binding protein-43 (TDP-43) function in an animal. The method comprises administering the agent to a non-human animal model as aforementioned; and determining whether the agent prevents and/or inhibits at least one of the ALS-like symptoms; wherein prevention and/or inhibition of the at least one of the ALS-like symptoms is indicative of an agent with potential for treatment of a disease associated with a loss of TDP-43 function.

Yet in another aspect, the invention relates to a method for identifying a candidate agent for treating, preventing and/or inhibiting ALS associated with a loss-of-function of TDP-43, in which the method comprises administering the agent to a non-human animal model as aforementioned; and determining whether the agent prevents and/or inhibits at least one of the ALS-like symptoms; wherein prevention and/or inhibition of the at least one of the ALS-like symptoms is indicative of a candidate agent for treating, preventing and/or inhibiting ALS associated with a loss-of-function of TDP-43.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIGS. 1A-1B are schematic representations depicting targeted disruption of Tardbp gene in the spinal cord motor neurons of a mouse. A. The exons 2 (E2) and 3 (E3) of TDP-43-encoding gene were replaced with a 'floxed' fragment containing exons 2 and 3 followed by a frt-flanking neo cassette. The neo cassette was then removed by germline expression of flp recombinase and the two exons were removed by HB9 promoter-driven Cre recombinase from Hb9-Cre mice. The genotypes of mice carrying different alleles were validated by PCR (primers a, b, and c) of their genomic DNAs from different tissues. B. Schematic illustration of the knockout strategy. The EIIa-Cre recombinase was expressed in all tissue cells and it deleted the DNA sequence between the two loxP sites in the $Tardbp^{1\times}$ allele. The resulting $Tardbp^{+/-}$ mice were crossed with $Tardbp^{1\times/+}$ mice to obtain $Tardbp^{1\times/-}$ mice. The $Tardbp^{1\times/-}$ mice were then crossed with HB9-Cre mice (with spinal cord motor neuron-specific expression of Cre recombinase) to generate the HB9-$Tardbp^{1\times/-}$ mice.

FIG. 5 shows accumulation of ubiquitinated proteins in the spinal cord motor neurons of the HB9-$Tardbp^{1\times/-}$ mice. The lumbar sections of the spinal cords of 20 week-old control (upper 2 rows of panels) and HB9-$Tardbp^{1\times/-}$ (lower 4 rows of panels) mice were immunofluorescence co-stained with anti-ubiquitin and anti-ChAT. DAPI staining indicated the locations of the nuclei. The patterns of one representative section of the control mice and two representative sections of the HB9-$Tardbp^{1\times/-}$ mice are shown. Note the increased anti-ubiquitin signals in the cytosol of ChAT-positive cells of the HB9-$Tardbp^{1\times/-}$ mice. The white curved line(s) indicates the boundary of the white matter and gray matter of the spinal cord. The boxes mark the regions of the ventral horn magnified for better visualization of the staining signals. N=4 for each group. The scale bars are 50 µm.

DETAILED DESCRIPTION OF THE INVENTION

Definitions

Figure 1B:
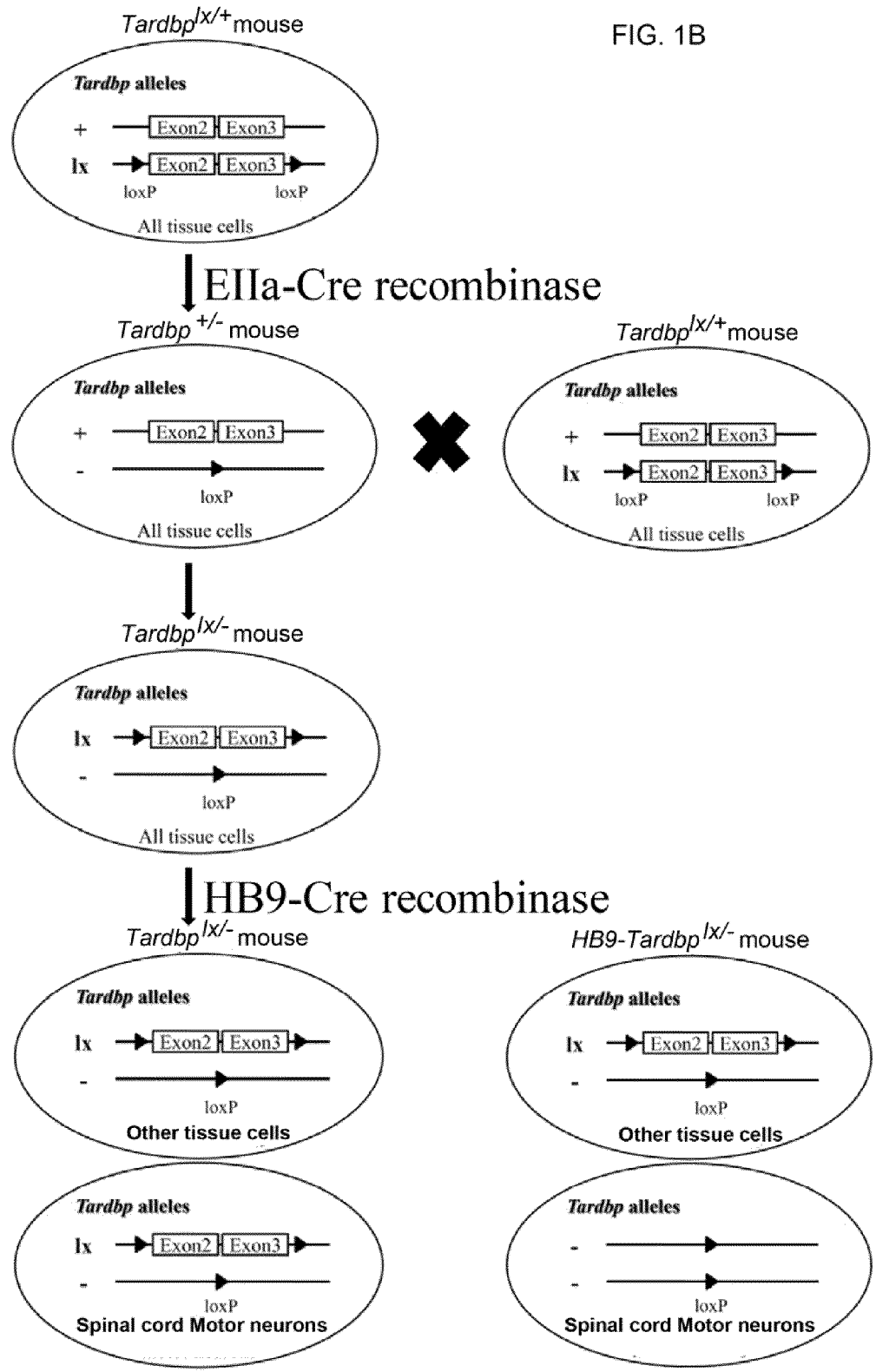

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms Used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, "a control mouse" shall generally mean a mouse whose spinal cord motor neurons do not have a loss of TDP-43 function.

A loss of TDP-43 function shall generally mean "reduced or abolished TDP-43 function." A loss of function generally results from no expression or abnormal expression of TDP-43-encoding gene, or inactivation of the gene product leading to less or no function of the gene.

The term "ALS-like symptoms" shall generally mean "symptoms associated with ALS." As used herein, "ALS-like symptoms comprises one or more than one of the following phenotypes: a) kyphosis; b) abnormal hind limb clasping; c) deficiency in motor coordination and motor learning ability or deficiency in rotorad test; d) motor neuron loss in the spinal cord; e) astrocytosis in the spinal cord; f) weight loss compared with a control rodent; and g) accumulation of polyubiquitinated proteins in the spinal cord motor neurons.

The term "expressing normal amount of TDP-43" means expressing TDP-43 in an amount similar to a control mouse.

The terms "HB9" and "Hb9" are interchangeable. Expression of Hb9 protein occurs primarily in the motor neurons of the spinal cord. The Hb9 promoter is used for spinal cord motor neuron-specific transgene expression. The motor neuron-specific Hb9 promoter is disclosed in Lee et al., (2004) "Analysis of embryonic motoneuron gene regulation: derepression of general activators function in concert with enhancer factors" *Development* (131): 3295-3306, which is incorporated herein by reference in its entirety.

Cre recombinase or the Cre (causes recombination) protein consists of 4 subunits and two domains: The larger carboxyl (C-terminal) domain, and smaller amino (N-terminal) domain. The total protein has 343 amino acids. The C domain is similar in structure to the domain in the Integrase family of enzymes isolated from lambda phage. This is also the catalytic site of the enzyme.

Lox P site (locus of X-over P1) is a site on the Bacteriophage P1 consisting of 34 bp. There exists an asymmetric 8 bp sequence in between with two sets of palindromic, 13 bp sequences flanking it. The detailed structure is as follows: ATAACTTCGTATA-GCATACAT-TATACGAAGTTAT (13 bp-8 bp-13 bp) (SEQ ID NO: 2).

The terms "Tardbp" and "TARDBP" are interchangeable.

The term "Tardbp$^{1×/+}$ mouse" refers to a mouse in which one copy of the TARDBP gene is normal (wild-type Tardbp allele) and the other copy of the TARDBP gene (or the other Tardbp allele) has two knock-in loxP sites flanking exons 2 and 3 of the TARDBP gene. When the Tardbp$^{1×/+}$ mouse is crossed with an indicated promoter driven-Cre recombinase transgenic mouse (e.g., Hb9-Cre transgenic mouse), the Cre recombinase can excise the target DNA that is flanked by the two lox P sites and generate a target gene knock-out allele. For example, when the Tardbp$^{1×/+}$ mouse has a Hb9 promoter driven-Cre recombinase, i.e., Hb9-Tardbp$^{1×/+}$, the Cre specifically knock out the exons 2 and 3 of the Tardbp allele, which is flanked by the two lox P sites, in spinal cord motor neurons, leading to spinal cord motor neuron-specific disruption of TARDBP gene. Tardbp$^{+/-}$ genotype is a heterozygote with one copy of normal TARDBP gene and the other copy of TARDBP gene being knocked out. Originally the Tardbp$^{+/-}$ mouse was generated by crossing a Tardbp$^{1×/+}$ mouse with an EIIa-promoter driven Cre recombinase transgenic mouse. EIIa promoter is a zygote stage-expressing promoter. Generally, EIIa promoter drives gene expression in all the tissues at the adult stage.

Hb9-Tardbp$^{1×/+}$ genotype refers to a heterozygote with one copy of normal TARDBP gene in the whole body and the other copy of TARDBP gene being specifically knocked out in motor neurons, i.e., motor neuron-specific knockout.

Hb9-Tardbp$^{1×/-}$ genotype refers to a mouse whose whole body has one copy of TARDBP gene being knocked out and whose motor neurons additionally has its second copy of TARDBP gene being knocked out. Thus, the Hb9-Tardbp$^{1×/-}$ mouse is heterozygous for the Tardbp allele knock-out in its whole body except in motor neurons. In the motor neurons, Tardbp allele knock-out is homozygote due to Hb9-specific knock-out (i.e., spinal cord motor neuron specific knock-out). Heterozygotes were viable and exhibited no obvious defective phenotype. To obtain the maximum Cre recombination efficiency, Hb9-Tardbp$^{1×/-}$ genotype was generated.

A "disrupted gene" refers to a gene having a deletion or addition in the coding region of the gene so that there is a partial or complete loss of the function associated with that gene.

Unless otherwise specified, the terms "polynucleotides", "nucleic acid" and "nucleic acid molecule" are interchangeably in the present context. Unless otherwise specified, the terms "peptide", "polypeptide" and "protein" are interchangeably in the present context. The term "sequence" may relate to polynucleotides, nucleic acids, nucleic acid molecules, peptides, polypeptides and proteins, depending on the context in which the term "sequence" is used. The terms "gene(s)", "polynucleotide", "nucleic acid sequence", "nucleotide sequence", or "nucleic acid molecule(s)" as used herein refers to a polymeric form of nucleotides of any length, either ribonucleotides or deoxyribonucleotides. The terms refer only to the primary structure of the molecule.

Thus, the terms "gene(s)", "polynucleotide", "nucleic acid sequence", "nucleotide sequence", or "nucleic acid molecule(s)" as used herein include double- and single-stranded DNA and RNA. They also include known types of modifications, for example, methylation, "caps", substitutions of one or more of the naturally occurring nucleotides with an analog.

A "coding sequence" is a nucleotide sequence, which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleotide sequences or genomic DNA, while introns may be present as well under certain circumstances.

The animal model disclosed here is the first animal model which has tissue-specific knockout of TDP-43 gene in spinal cord motor neurons and exhibits major pathological symptoms of ALS.

The invention relates to the discovery that a loss of TDP-43 function in the spinal cord motor neurons is sufficient to cause ALS, and could be the major cause for the development of ALS. The implication of this finding is vital. In 90% of the ALS patients, it is still unknown as to which gene or genes causing ALS. Only 5% of the ALS patients are related to SOD1 and FUS/TLS gene mutations, in which the diseased cells have no TDP-43 aggregates. Even though the disease gene for causing ALS is unknown in more than 90% of the ALS patients, 80-90% of the ALS patients have TDP-43 aggregates in the diseased cells, indicating that TDP-43 protein are associated with 90% of the ALS cases. Therefore, the non-human animal model with a loss of TDP-43 function disclosed here is well suitable for studying these 90% of the ALS patients.

In addition, the non-human animal model of the invention is useful for drug screening, identification, and/or validation, etc.

In one aspect, the invention relates to a non-human animal model for amyotrophic lateral sclerosis (ALS), in which the animal model comprises a rodent whose spinal cord motor neurons have a loss of TAR-DNA binding protein-43 (TDP-43) function and the rodent exhibits ALS-like symptoms.

In another aspect, the invention relates to a tissue or a motor neuron which is isolated from the spinal cord of the animal model as aforementioned.

Further in another aspect, the invention relates to a method for identifying an agent with potential for treatment of a disease associated with a loss of TAR-DNA binding protein-43 (TDP-43) function in an animal. The method comprises administering the agent to a non-human animal model according to claim 1; and determining whether the agent prevents and/or inhibits at least one of the ALS-like symptoms; wherein prevention and/or inhibition of the at least one of the ALS-like symptoms is indicative of an agent with potential for treatment of a disease associated with a loss of TDP-43 function.

Yet in another aspect, the invention relates to a method for identifying a candidate agent for treating, preventing and/or inhibiting ALS associated with a loss-of-function of TDP-43, in which the method comprises administering the agent to a non-human animal model as aforementioned; and determining whether the agent prevents and/or inhibits at least one of the ALS-like symptoms; wherein prevention and/or inhibition of the at least one of the ALS-like symptoms is indicative of a candidate agent for treating, preventing and/or inhibiting ALS associated with a loss-of-function of TDP-43.

In one embodiment of the invention, the rodent does not express TDP-43 protein in the spinal cord motor neurons.

In another embodiment of the invention, the rodent expresses TDP-43 protein in the cells other than the spinal cord motor neurons.

In another embodiment of the invention, the rodent's TDP-43-encoding gene in the spinal cord motor neurons is inactivated.

In another embodiment of the invention, the rodent's TDP-43-encoding gene in the spinal cord motor neurons is inactivated and/or deleted.

In another embodiment of the invention, the rodent's TDP-43-encoding gene in the spinal cord motor neurons comprises a homozygous disruption.

In another embodiment of the invention, the rodent expresses Cre recombinase in the spinal cord motor neurons, but not in other cells.

In another embodiment of the invention, the Cre recombinase is driven by HB9 promoter.

In another embodiment of the invention, the rodent comprises Lox P sites in its genome, and the cells other than the spinal cord motor neurons in the rodent comprise a TDP-43-encoding gene with a pair of Lox P sites.

In another embodiment of the invention, the rodent is phenotypically normal at birth and develops the ALS-like symptoms later.

In another embodiment of the invention, the rodent's spinal cord motor neurons comprise ubiquitinated protein aggregates.

In another embodiment of the invention, the rodent exhibits a loss of spinal cord motor neurons.

In another embodiment of the invention, the animal model exhibits one or more than one of the following phenotypes: a) kyphosis; b) abnormal hind limb clasping; c) deficiency in motor coordination and motor learning ability; d) motor neuron loss in the spinal cord; e) astrocytosis in the spinal cord; f) weight loss compared with a control rodent; and g) accumulation of poly-ubiquitinated proteins in the spinal cord motor neurons.

In another embodiment of the invention, the exon 2 and exon 3 of TDP-43-encoding gene in the rodent's spinal cord motor neurons are deleted.

In another embodiment of the invention, the motor neuron comprises ubiquitinated protein aggregates and having no TDP-43 protein expression.

In another embodiment of the invention, the animal model is a mouse.

The non-human animal model of the invention differs from the ALS mouse models reported in art. SOD1 transgenic mice do not have a loss of TDP-43 function. Instead, SOD1 transgenic mice overexpress mutant SOD1 protein, which harbors ALS-associated mutation in Gly93Ala (G93A). Their diseased cells have protein aggregates which contain normal SOD1 and mutant SOD1 (SOD1G93A) but not TDP-43 aggregates. Mutation of SOD1 gene accounts for only 4% of ALS patients. The SOD1 transgenic mouse model is therefore not suitable for studying 80-90% of the ALS patient cases, in which TDP-43 aggregates are present in the diseased cells.

ALS-2 knockout mice exhibit a severe form of hereditary spastic paralysis, which is quite distinct from ALS. In addition, the mutation of ALS-2 causes ALS mainly by gain-of-toxicity function, not by loss-of-function. Those gene knockout mice are therefore not suitable for studying ALS, or screening/identification of drugs for treatment of ALS.

The animal model disclosed here also differs from the TDP-43 transgenic mouse, in which TDP-43 is overexpressed.

The art knows how to generate a loss-of-function in an organism. For example, the loss-of-function of TDP-43 could be achieved by gene knock out (e.g., with HB-9-Cre, modified Crc, etc.), RNA interference (RNAi) and inactivation of TDP-43 protein by using chemicals, drugs, etc. Inactivation of a gene product may also be achieved by using microRNAs (miRNAs) to degrade TDP-43 mRNA or inhibit translation of TDP-43. mRNA. Below illustrates some of the examples of methods for generating a loss-of-function.

Antisense Method

Methods for suppressing a specific protein by preventing the accumulation of its mRNA by means of "antisense" technology have been described extensively (U.S. Pat. No. 7,951, 565, which is herein incorporated by reference in its entirety). The antisense nucleic acid molecule hybridizes with, or binds to, the cellular mRNA and/or the genomic DNA encoding the target protein to be suppressed. This process suppresses the transcription and/or translation of the target protein. Hybridization can be brought about in a conventional manner via the formation of a stable duplex or, in the case of genomic DNA, by the antisense nucleic acid molecule binding to the duplex of the genomic DNA by specific interaction in the large groove of the DNA helix.

An "antisense" nucleic acid molecule comprises a nucleotide sequence, which is at least in part complementary to a "sense" nucleic acid molecule encoding a protein, e.g., complementary to the coding strand of a double-stranded cDNA molecule or complementary to an encoding mRNA sequence. Accordingly, an antisense nucleic acid molecule can bind via hydrogen bonds to a sense nucleic acid molecule. The antisense nucleic acid molecule can be complementary to an entire coding strand of a nucleic acid molecule conferring the expression of the polypeptide or to only a portion thereof. Accordingly, an antisense nucleic acid molecule can be antisense to a "coding region" of the coding strand. The term "coding region" refers to the region of the nucleotide sequence comprising codons, which are translated into amino acid residues. Further, the antisense nucleic acid molecule is antisense to a "noncoding region" of the mRNA flanking the coding region of a nucleotide sequence. The term "noncoding region" refers to 5' and 3' sequences which flank the coding region that are not translated into a polypeptide, i.e., also referred to as 5' and 3' untranslated regions (5'-UTR or 3'-UTR). An antisense nucleic acid sequence which is suitable for reducing the activity of a protein can be deduced using the nucleic acid sequence encoding this protein.

The antisense nucleic acid molecules are typically administered to a cell or generated in situ such that they hybridize with or bind to cellular mRNA and/or genomic DNA encoding a polypeptide having the biological activity of protein thereby inhibit expression of the protein, e.g., by inhibiting transcription and/or translation.

The antisense molecule comprises also a nucleic acid molecule comprising a nucleotide sequences complementary to the regulatory region of TDP-43, e.g., its promoter and/or enhancers, e.g. to form triple helical structures that prevent transcription of the gene in target cells.

Antisense Combined with a Ribozyme

It is advantageous to combine the above-described antisense strategy with a ribozyme method. Catalytic RNA molecules or ribozymes can be adapted to any target RNA and cleave the phosphodiester backbone at specific positions, thus functionally deactivating the target RNA. The ribozyme per se is not modified thereby, but is capable of cleaving further target RNA molecules in an analogous manner, thus acquiring the properties of an enzyme. The incorporation of ribozyme sequences into "antisense" RNAs imparts this enzyme-like RNA-cleaving property to precisely these "antisense" RNAs and thus increases their efficiency when inactivating the target RNA. The preparation and the use of suitable ribozyme "antisense" RNA molecules is described, for example, by Haseloff et al. (1988) Nature 33410: 585-591.

Ribozymes are catalytic RNA molecules with ribonuclease activity, which are capable of cleaving a single-stranded nucleic acid, such as an mRNA, to which they have a complementary region. In this manner, ribozymes can be used to catalytically cleave the mRNA of a protein to be suppressed and to prevent translation. The ribozyme technology can increase the efficacy of an anti-sense strategy. Methods for expressing ribozymes for reducing specific proteins are described in (EP 0 291 533, EP 0 321 201, EP 0 360 257). Suitable target sequences and ribozymes can be identified for example as described by Steinecke P, Ribozymes, Methods in Cell Biology 50, Galbraith et al. eds, Academic Press, Inc. (1995), pp. 449-460 by calculating the secondary structures of ribozyme RNA and target RNA and by their interaction [Bayley C C et al. (1992) Plant Mol. Biol. 18(2): 353-361; Lloyd A M and Davis R W et al. (1994) Mol. Gen. Genet. 242(6): 653-657].

Sense for Inducing Cosuppression

The expression of a nucleic acid sequence in sense orientation can lead to cosuppression of the corresponding homologous, endogenous genes. The expression of sense RNA with homology to an endogenous gene can reduce or indeed eliminate the expression of the endogenous gene, in a similar manner as has been described for the following antisense approaches: Jorgensen et al. [(1996) Plant Mol. Biol. 31(5): 957-973], Goring et al. [(1991) Proc. Natl. Acad. Sci. USA 88: 1770-1774], Smith et al. [(1990) Mol. Gen. Genet. 224: 447-481], Napoli et al. [(1990) Plant Cell 2: 279-289] or Van der Krol et al. [(1990) Plant Cell 2: 291-99]. In this context, the construct introduced may represent the homologous gene to be reduced either in full or only in part. Furthermore the above described cosuppression strategy can advantageously be combined with the RNAi method as described by Brummell et al., 2003, Plant J. 33, pp 793-800.

MicroRNAs and siRNA

MicroRNAs (miRNAs) are short ribonucleic acid (RNA) molecules, on average only 22 nucleotides long, which regulate gene expression. The mature miRNA is part of an active RNA-induced silencing complex (RISC) containing Dicer and many associated proteins. RISC is also known as a microRNA ribonucleoprotein complex (miRNP); RISC with incorporated miRNA is sometimes referred to as "miRISC." Gene silencing may occur either via mRNA degradation or preventing mRNA from being translated.

Small interfering RNA (siRNA), or short interfering RNA or silencing RNA, is a class of double-stranded RNA molecules, 20-25 nucleotides in length. siRNA is involved in the RNA interference (RNAi) pathway, where it interferes with the expression of a specific gene. An exogenous RNA may be a long strand designed to be cleaved by dicer, or short RNAs designed to serve as siRNA substrates.

Nucleic Acid Sequences Encoding a Dominant-Negative Protein

The function or activity of a protein can efficiently also be reduced by expressing a dominant-negative variant of said protein. The skilled worker is familiar with methods for reducing the function or activity of a protein by means of coexpression of its dominant-negative form [Lagna G and Hemmati-Brivanlou A (1998) Current Topics in Developmental Biology 36: 75-98; Perlmutter R M and Alberola-IIa J (1996) Current Opinion in Immunology 8(2): 285-90; Sheppard D (1994) American Journal of Respiratory Cell & Molecular Biology 11(1): 1-6; Herskowitz I (1987) Nature 329 (6136): 219-22].

DNA- or Protein-Binding Factors Against Genes, RNAs or Proteins

A reduction in the expression of a gene can also be achieved with specific DNA-binding factors, for example factors of the zinc finger transcription factor type. These factors attach to the genomic sequence of the endogenous target gene, preferably in the regulatory regions, and bring about repression of the endogenous gene. The use of such a method makes possible the reduction in the expression of an endogenous gene without it being necessary to recombinantly manipulate the sequence of the latter. Such methods for the preparation of relevant factors are described previously (U.S. Pat. No. 7,951,565, which is herein incorporated by reference in its entirety).

These factors can be selected using any portion of a gene. This segment is preferably located in the promoter region. For the purposes of gene suppression, however, it may also be located in the region of the coding exons or introns.

Viral Nucleic Acid Sequences and Expression Constructs for Degradation of RNA

Inactivation or downregulation can also be efficiently brought about by inducing specific RNA degradation by the organism, with the aid of a viral expression system (Amplikon) [Angell, S M et al. (1999) Plant J. 20(3): 357-362]. Nucleic acid sequences with homology to the transcripts to be suppressed are introduced into the organism by these systems—also referred to as "VIGS" (vital induced gene silencing) with the aid of viral vectors. Then, transcription is switched off, presumably mediated by organism defense mechanisms against viruses. Suitable techniques and methods are described in Ratcliff F et al. [(2001) Plant J. 25(2): 237-45], Fagard M and Vaucheret H [(2000) Plant Mol. Biol.

43 (2-3): 285-93], Anandalakshmi R et al. [(1998) Proc. Natl. Acad. Sci. USA 95(22): 13079-84] and Ruiz M T [(1998) Plant Cell 10(6): 937-46].

Constructs for Inducing a Homologous Recombination on Endogenous Genes for Generating Knock-Out Mutants A multiplicity of sequence-specific recombination systems may be used, examples including Cre/lox system of bacteriophage P1, the FLP/FRT system from yeast, the Gin recombinase of phage Mu, the Pin recombinase from E. coli and the R/RS system of the pSR1 plasmid. The Bacteriophage P1 Cre/lox system and the yeast FLP/FRT system are preferred. The FLP/FRT and the cre/lox recombinase system have already been applied to plant systems [Odell et al. (1990) Mol. Gen. Genet. 223: 369-378].

A gene knockout is a genetic technique in which one of an organism's genes is made inoperative ("knocked out" of the organism). Also known as knockout organisms or simply knockouts, they are used in learning about a gene that has been sequenced, but which has an unknown or incompletely known function. Researchers draw inferences from the difference between the knockout organism and normal individuals. The term also refers to the process of creating such an organism, as in "knocking out" a gene.

Knockout is accomplished through a combination of techniques, beginning in the test tube with a plasmid, a bacterial artificial chromosome or other DNA construct, and proceeding to cell culture. Individual cells are genetically transformed with the DNA construct. Often the goal is to create a transgenic animal that has the altered gene. If so, embryonic stem cells are genetically transformed and inserted into early embryos. Resulting animals with the genetic change in their germline cells can then often pass the gene knockout to future generations.

The construct is engineered to recombine with the target gene, which is accomplished by incorporating sequences from the gene itself into the construct. Recombination then occurs in the region of that sequence within the gene, resulting in the insertion of a foreign sequence to disrupt the gene. With its sequence interrupted, the altered gene in most cases will be translated into a nonfunctional protein, if it is translated at all.

A conditional knockout allows gene deletion in a tissue or time specific manner. This is done by introducing short sequences called loxP sites around the gene. These sequences will be introduced into the germ-line via the same mechanism as a knock-in. This germ-line can then be crossed to another germline containing Cre-recombinase which is a viral enzyme that can recognize these sequences, recombines them and deletes the gene flanked by these sites.

Because the desired type of DNA recombination is a rare event in the case of most cells and most constructs, the foreign sequence chosen for insertion usually includes a reporter. This enables easy selection of cells or individuals in which knockout was successful. Sometimes the DNA construct inserts into a chromosome without the desired homologous recombination with the target gene. To eliminate such cells, the DNA construct often contains a second region of DNA that allows such cells to be identified and discarded.

In diploid organisms, which contain two alleles for most genes, and may as well contain several related genes that collaborate in the same role, additional rounds of transformation and selection are performed until every targeted gene is knocked out. Selective breeding may be required to produce homozygous knockout animals.

Loss of Function Mutation (For Example Generation of Stop Codons Reading-Frame Shifts and the Like)

Further suitable methods for reducing activity are the introduction of nonsense mutations into endogenous genes, for example by introducing RNA/DNA oligonucleotides into the organism [Zhu et al. (2000) Nat. Biotechnol. 18(5): 555-558], and the generation of knock-out mutants with the aid of, for example, T-DNA mutagenesis [Koncz et al. (1992) Plant Mol. Biol. 20(5): 963-976], ENU-(N-ethyl-N-nitrosourea)—mutagenesis or homologous recombination [Hohn B and Puchta (1999) H. Proc. Natl. Acad. Sci. USA 96: 8321-8323]. Point mutations may also be generated by means of DNA-RNA hybrids also known as "chimeraplasty" [Cole-Strauss et al. (1999) Nucl. Acids Res. 27(5): 1323-1330; Kmiec (1999) Gene Therapy American Scientist 87(3): 240-247]. The mutation sites may be specifically targeted or randomly selected. If the mutations have been created randomly e.g. by Transposon-Tagging or chemical mutagenesis, the skilled worked is able to specifically enrich selected mutation events.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods

Animals

C57BL/6J strain mice were Used in this study. All animals were maintained in a specific pathogen-free environment under standard laboratory conditions and handled following the guidelines of the institutional animal committee.

The Tardbp allele was knocked out specifically in the post-mitotic motor neurons in the spinal cord by crossing mice carrying the Tardbp conditional allele (Tardbp$^{1\times}$) with mice carrying a Cre-recombinase transgene driven by the HB9-promoter (HB9-Cre). The viabilities and weights of the mice were monitored regularly. Genotyping of the mice was performed by PCR of genomic DNAs from the tail biopsies in comparison to the nail samples.

Gene Targeting

The removal of the genomic regions was achieved by standard gene-targeting approach using the Cre-lox recombination system. The targeting vector was generated by deletion of exons 2 and 3 of Tardbp in the BAC clone RP23-364M1 (Invitrogen) with use of the counter-selection BAC modification kit (Gene bridges). A loxP site was inserted at 473 bp before the exon 2 of Tardbp. A frt site flanking the PGK-neo cassette followed by another loxP site was inserted at 637 bp behind exon 3. A 29 bp region in front of the PGK-neo cassette was deleted on the targeting vector for ES cell screening. To achieve the homologous recombination, the targeting vector was electroporated into C57BL/6J ES cells. G418-resistant ES cell clones were genotyped by PCR with an intensity comparison method. Two independent targeted ES cell clones were expanded and microinjected into C57BL/6-C2J blastocysts to generate the chimeric mice, which were then mated with the wild type C2J C57BL/6J albino mice.

The neo cassette in the targeted Tardbp locus was removed by crossing the germline transmitting F1 lines Tardbp$^{1x}$ mice with FLPe mice (Rodriguez et al. (2000) "High-efficiency deleter mice show that FLPe is an alternative to Cre-loxP" *Nat Genet* 25, 139-140). To obtain the heterozygous mice containing the deleted allele (Tardbp$^{+/-}$), the Tardbp$^{1x}$ mice were crossed with EIIa-Cre mice expressing the Cre recombinase in the whole body (Lakso et al. (1996) "Efficient in vivo manipulation of mouse genomic sequences at the zygote stage" *Proc Natl Acad Sci USA* 93, 5860-5865). To obtain the motoneuron-specific-deficient mice, the Tardbp$^{1x}$ mice were crossed with HB9-Cre transgenic mice which were purchased from Jackson Laboratory (stock #: 006600). To obtain the maximum recombination, the Hb9-Tardbp$^{1x/+}$ were then crossed to Tardbp$^{+/-}$ to achieve motoneuron-specific-deficient Hb9-Tardbp$^{1x/-}$ mice. The mice used for this study were kept on a C57BL/6J genetic background.

Phenotyping of the Disease Mice

The clinical conditions of the mice were monitored three times per week. Onset of the disease was determined by the developments of kyphosis of the mouse and their limb shaking when being suspended in the air by tails. For the limb-clasping test, the mice were suspended by pulling their tails. For the rotarod test, the mice were trained before testing to exclude differences in motivation and motor learning. Mice were first trained for four consecutive days. In the testing phase, they were put on the rod rotating constantly at 2.5 rpm, and the speed was gradually increased to 25 rpm over a 3-min period. The timer was stopped when the mice fell from the rod or when they gripped the rod and started to rotate with it.

Tissue Preparation and Staining

Mice were sacrificed under deep anaesthesia, and perfused transcardially with 4% paraformaldehyde in PBS (pH 7.4). The spinal cords were dissected and the lumber segments (L3-L6) were identified using the ribs and the vertebrae as a guide. The segments were processed for cryoprotection, and 100 serial cross-sections were made of the lumbar spinal cords at a thickness of 10 µm. Every twelfth section (a total of 12 sections from each animal) was stained with 1% cresyl violet (Sigma). Each section was visualized with an Axioimage-Z1 light microscope at 20× magnification, and the cells were counted manually by tracing the perimeter of each motor neuron. The cell counts were made within an area demarcated by a horizontal line drawn through the central canal and encompassing the ventral horn of the grey matter to include layers 7-9. The cell areas of motor neurons were identified and analyzed using the following criteria: (1) the presence of a large nucleolus located within the nucleus surrounded by light blue-staining cytoplasm; and (2) a cell soma area over 100 µm². The gamma (γ) motor neurons range in their soma areas from 100 to 250 µm², whereas the soma areas of the larger alpha (α) motor neurons range from 250 to 1100 µm².

In a parallel set of the sections, the motor neurons were identified by immunostaining with different antibodies: a goat antibody directed against the choline acetyltransferase (ChAT; Chemicon), a rabbit anti-TDP-43 (Proteintech), a rabbit anti-GFAP (Milopore), a mouse anti-MAP2 (Sigma), a rabbit anti-ubiquitin (Dako). The section were pre-incubated in PBS solution containing 10% (vol/vol) normal donkey serum and 0.2% Triton X-100 for 1 h, and then incubated overnight with one or more of the antibodies. Antibody against the rabbit/mouse IgG (Jackson ImmunoResearch) was used for secondary detection. The images were taken from the ZEISS-LSM710 and LSM780 confocal microscopy.

Results and Discussion

Generation of Mice with Conditional Knockout of Tardbp Expression in the Spinal Cord Motor Neurons To investigate whether loss of TDP-43 function in motor neurons would lead to the development of the ALS disease phenotype, the Tardbp gene in motor neurons was inactivated by using a Cre-loxP recombination system. A conditional allele of the Tardbp locus was generated by flanking exons 2 and 3 with loxP sites (Tardbp$^{1x}$ allele), which was suitable for Cre-mediated Tardbp floxed gene inactivation (FIG. 1A). To generate a null allele of the Tardbp gene (Tardbp+/−), the Tardbp1x/+ mice were first crossed with EIIa-Cre mice which expressed Cre recombinase in all tissues. These mice (Tardbp+/−) were then crossed with the Tardbp1x/+ mice to obtain the Tardbp1x/− mice. These mice (Tardbp1/−) were further crossed with motor neuron-specific Mnx1 (HB9)-Cre mice to generate the HB9-Tardbp1x/− mice (FIGS. 1A and 1B). HB9 is a homeodomain transcription factor that is expressed selectively in motor neurons in the developing spinal cord (E9.5) and is essential for differentiation of the post-mitotic motor neurons. HB9-Cre mice express the Cre gene specifically in the spinal cord motor neurons and have been used previously to manipulate gene expression in the motor neurons. The specificity of the Cre recombination in our mice was confirmed by crossing the HB9-Cre mice with Rosa26-GFP fox transgenic mice so that the expression of the GFP gene in the latter mice could be activated only upon the Cre recombination.

Figure 2A:
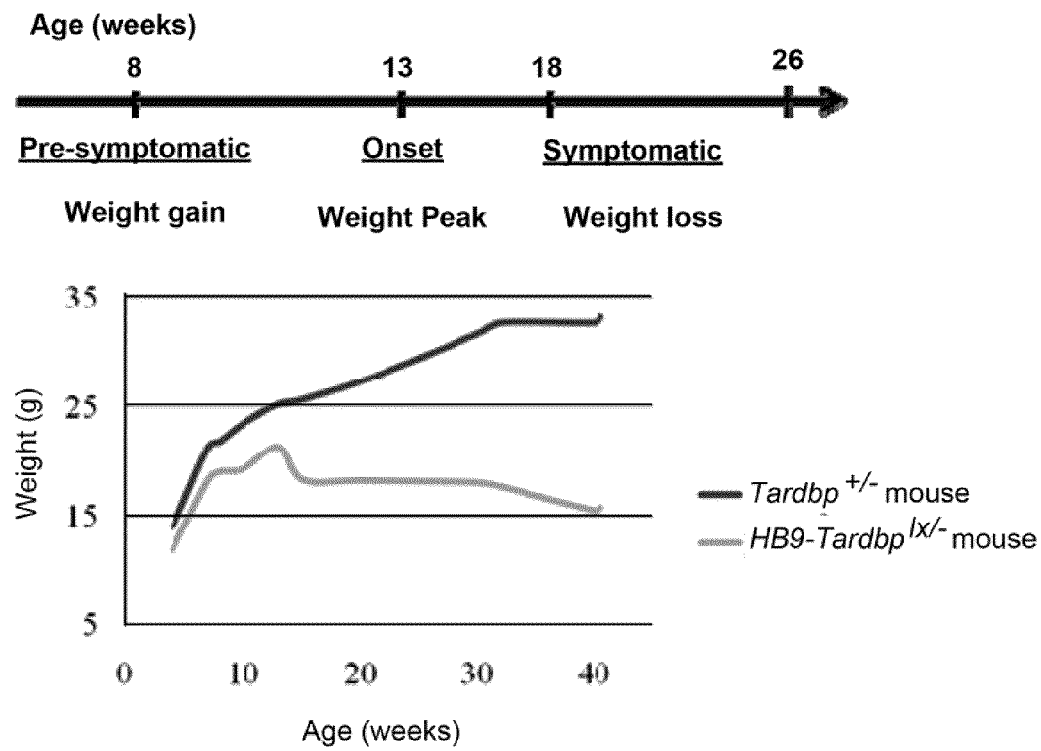
FIGS. 2A-2D show ALS-like phenotypes of HB9-$Tardbp^{1\times/-}$ mice. A. Top, time scale of the progression of ALS-like phenotypes of the HB9-$Tardbp^{1\times/-}$ mice, as exemplified in 2A-2D. Below, typical weight curves. The disease onset of the HB9-$Tardbp^{1\times/-}$ mice is defined as the start of the weight loss at around 13 weeks. B. Hindlimb clasping test. Abnormal clasping of a 20 week-old HB9-$Tardbp^{1\times/-}$ mouse is exemplified in the right panel as compared to a control littermate in the left panel. C. Rotarod test. The indices (time on the rotarod after normalization to the control) are plotted against the ages of the mice. D. Kyphosis phenotype of the mutant mouse (right panels) in comparison with the control (left panels) at 20 weeks of age. The lower 4 panels are the contrast enhancement radiographs of the skeletons. N=6 for each group.
Figure 2B:
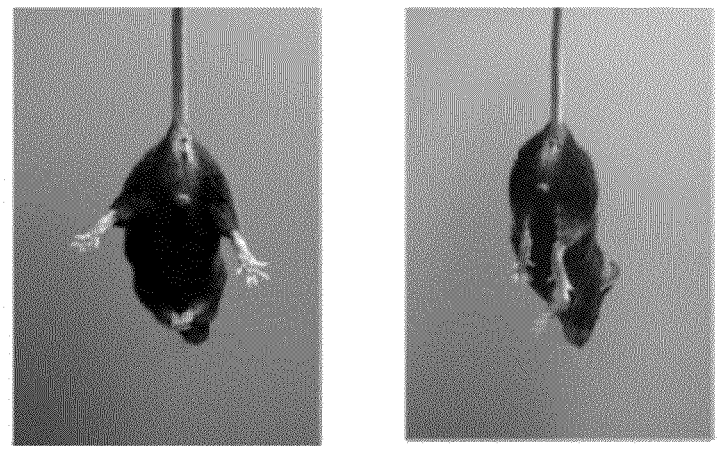
Figure 2C:
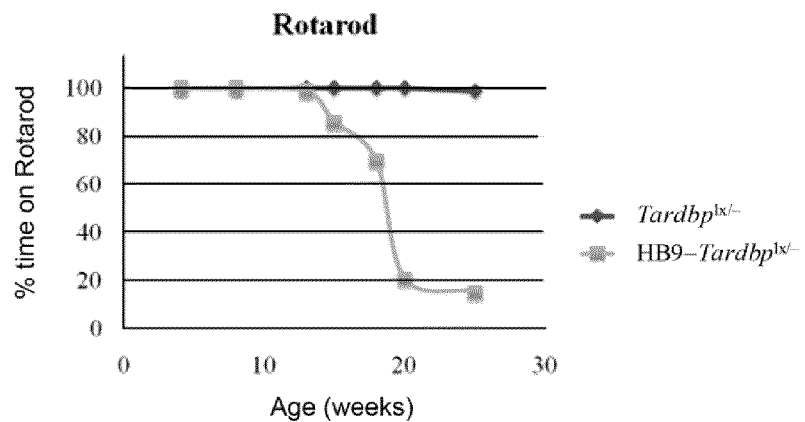

Development of ALS-Like Morphological and Behavioral Phenotypes in HB9-Tardbp$^{1x/-}$ Mice Unlike the EIIa-Tardbp1x/1x mice generated previously, which were lethal at the peri-implantation stage, HB9-Tardbp1x/− mice were viable and phenotypically normal at birth, suggesting that TDP-43 was not essential for normal development of the spinal cord motor neurons. However, although the average weight of the HB9-Tardbp1x/− mice was only slightly lower than the controls at early births, the difference became more prominent afterwards (FIG. 2A). The body weight was shown previously to be a simple and reliable measure for the disease 'onset' and progression in the ALS mouse model with transgenic expression of the mutant human hSOD1 (G93A), with the inflection point of the weight curve providing a simple definition of the disease onset. Similar to the mutant hSOD1Tg mice, HB9-Tardbp1x/− mice also showed a peak of weight-gain during 90 to 100 days (~13 weeks, FIG. 2A). Soon after that, the mice started to show significant weight loss (FIG. 2A), abnormal hind limb clasping (FIG. 2B), and deficiency in rotarod test (FIG. 2C).

Figure 2D:
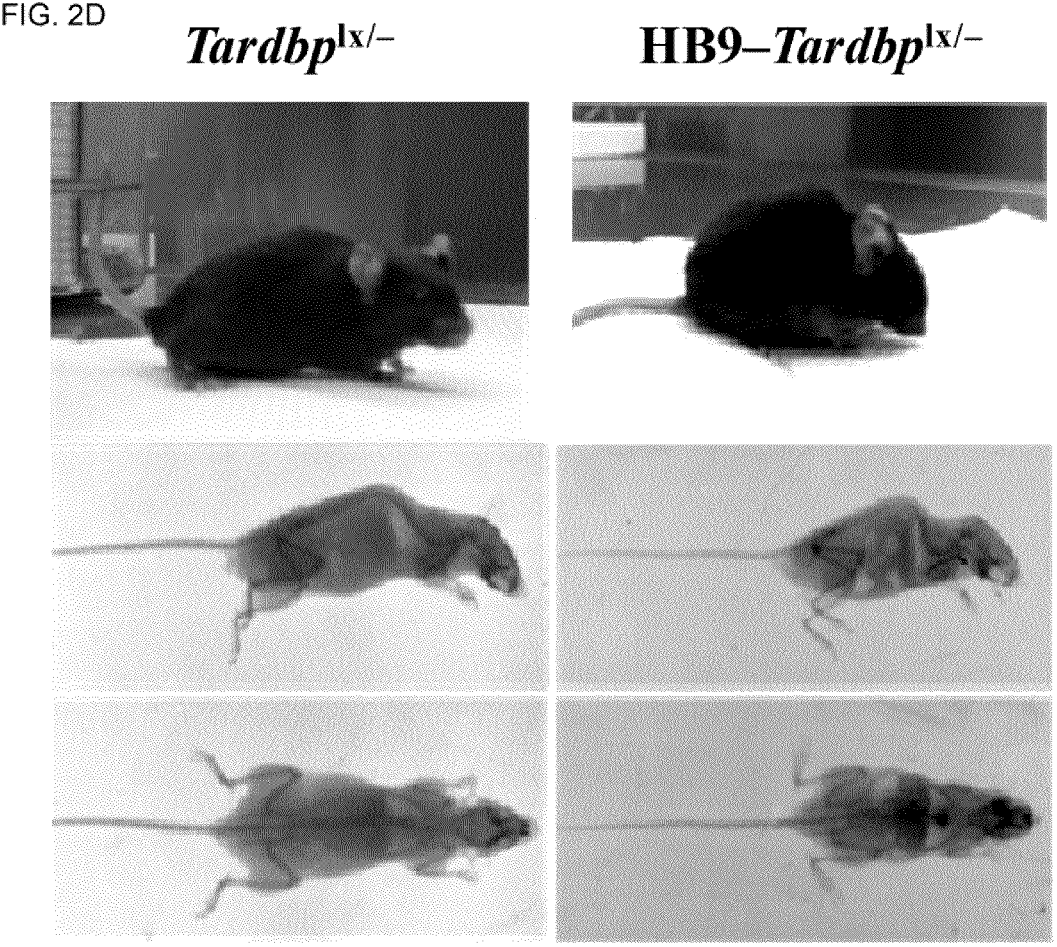

Although all of the above clinical signs were similar between the HB9-Tardbp1x/− mice and the mutant hSOD1 Tg mice, the disease progression after the symptom onset was somewhat slower in the HB9-Tardbp1x/− mice. Interestingly, the HB9-Tardbp1x/− mice exhibited a kyphosis phenotype beginning at 20 weeks of age and it became severe at 24 weeks, as exemplified in FIG. 2D. The kyphosis likely resulted from weakening of the extensor thoracic paraspinal muscles, as observed in the ALS patients as well as in the mutant hSOD1 (G93A) Tg mice. Finally, similar to ALS, the development of ALS-like phenotypes in HB9-Tardbp1x/− mice was also male-dominant, with a male/female ratio of 3:1. The average life span of the HB9-Tardbp1x/− mice showing ALS-like phenotypes was 10 months.

Figure 3A:
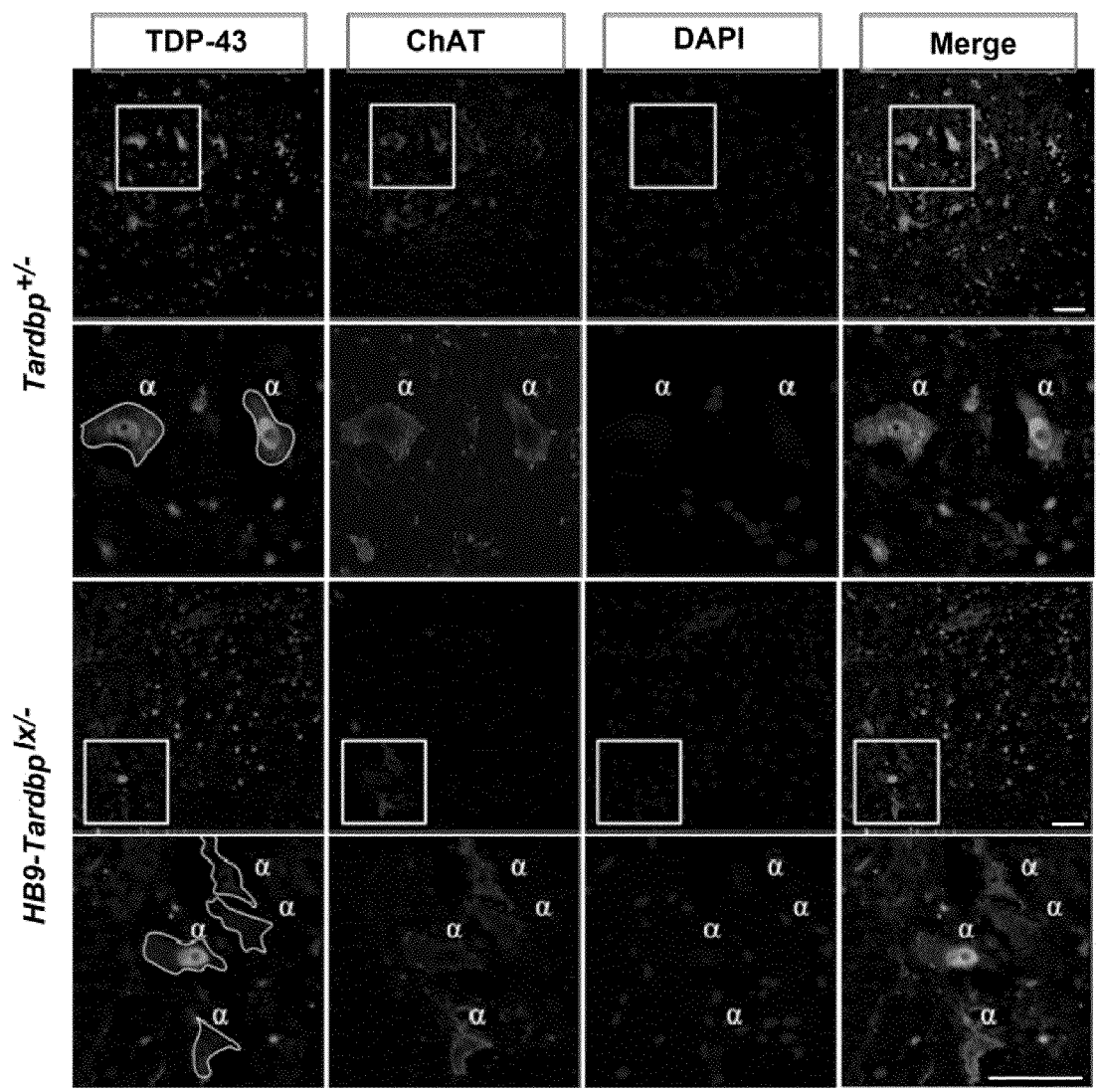
FIG. 3 shows motor neuron loss in the spinal cords of the HB9-$Tardbp^{1\times/-}$ mice. A. Immunofluorescence co-staining of ChAT and TDP-43 showing that the number of ChAT-positive motor neurons (MN) in the lumbar spinal cord of the HB9-$Tardbp^{1\times/-}$ mice (lower two rows of panels) is reduced in comparison with the control (upper two rows). The scale bar is 50 µm. C. The quantitative comparison is shown by the bar histogram. Note the depletion of TDP-43 in most, although not all, of the ChAT(+) cells or motor neurons. B. Top, photomicrographs showing the cresyl violet (Nissl)-stained sections through the ventral horn of the lumbar spinal cord from a HB9-$Tardbp^{1\times/-}$ mouse at the age of 20 weeks (upper two panels, i and ii) in comparison with a control littermate (lower two panels, iii and iv). The scale bar is 50 µm. D. the quantitative analysis is presented by the bar histogram. Note the reduction in the numbers of both α motor neurons (white bars, 60%) and γ motor neurons (gray bars, 40%) in the mutant mice. N=4 for each group.
Figure 3B:
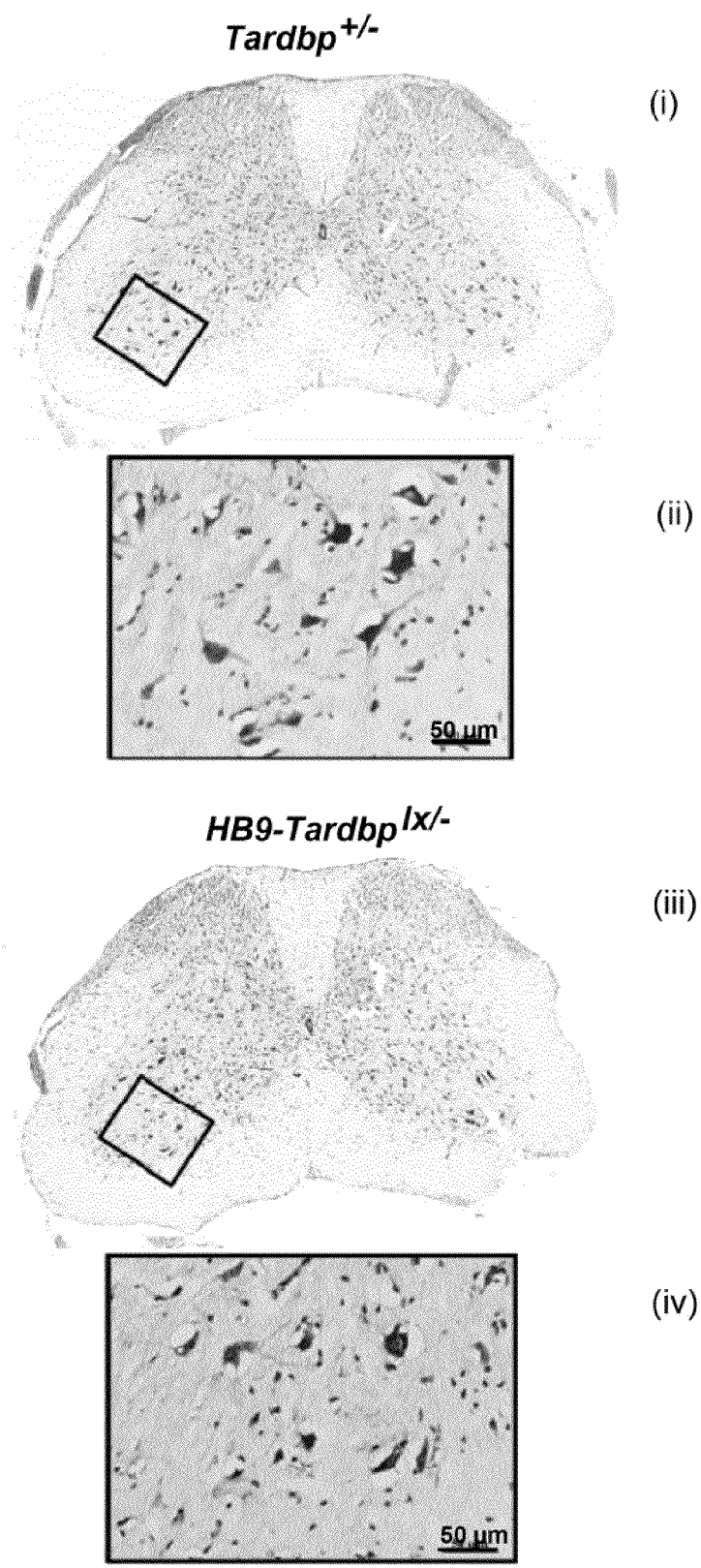
Figure 3C:
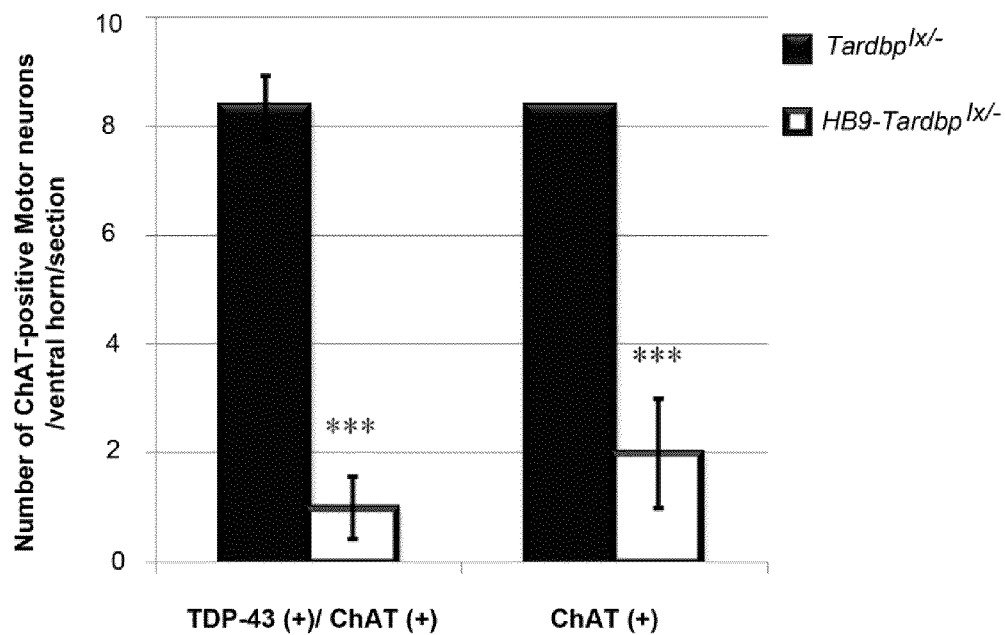

Motor Neuron Loss, Enhancement of Astrocytosis and Accumulation of Ubiquitinated proteins in the Spinal Cord of HB9-Tardbp1x/−Mice ALS was defined as a neurodegenerative disorder characterized by progressive muscle weakness indicating the degeneration of motor neurons in the primary motor cortex, brainstem and spinal cord. Progressive atrophy of the muscle fibers, which were denervated as their corresponding motor neurons degenerated, leads to weakening of the affected muscles. It was reasoned that the restricted population of the spinal cord motor neurons in the HB9-Tardbp1x/− mice might be affected by the depletion of TDP-43. Indeed, histology analysis of the spinal cords showed a decrease of ChAT-positive motor neurons among the ventral horn cells of 20 weeks old HB9-Tardbp1x/− mice (FIG. 3A). Furthermore, among the remaining ChAT-positive motor neurons of HB9-Tardbp1x/− mice, 66% had lost the immunostaining signals of TDP-43 (FIGS. 3A and 3C). FIG. 3C shows that in the ALS mice, the ChAT-positive cells in the spinal cord reduced by 76%. Among the remaining ChAT-positive cells, 50% of cells lost TDP-43 expression. In FIG. 3C, the label "TDP-43(+)/ChAT(+)" stands for double standing with TDP-43 and ChAT.

Figure 3D:
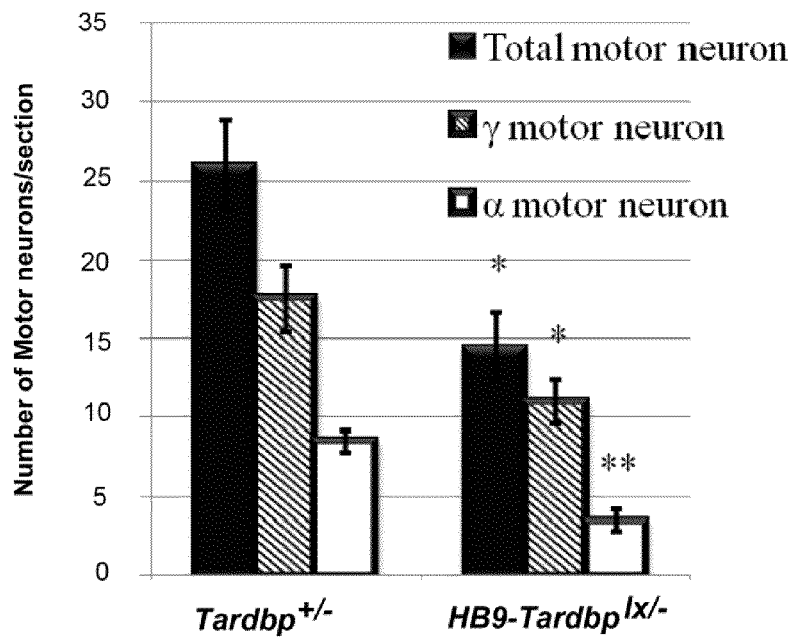
Figure 4:
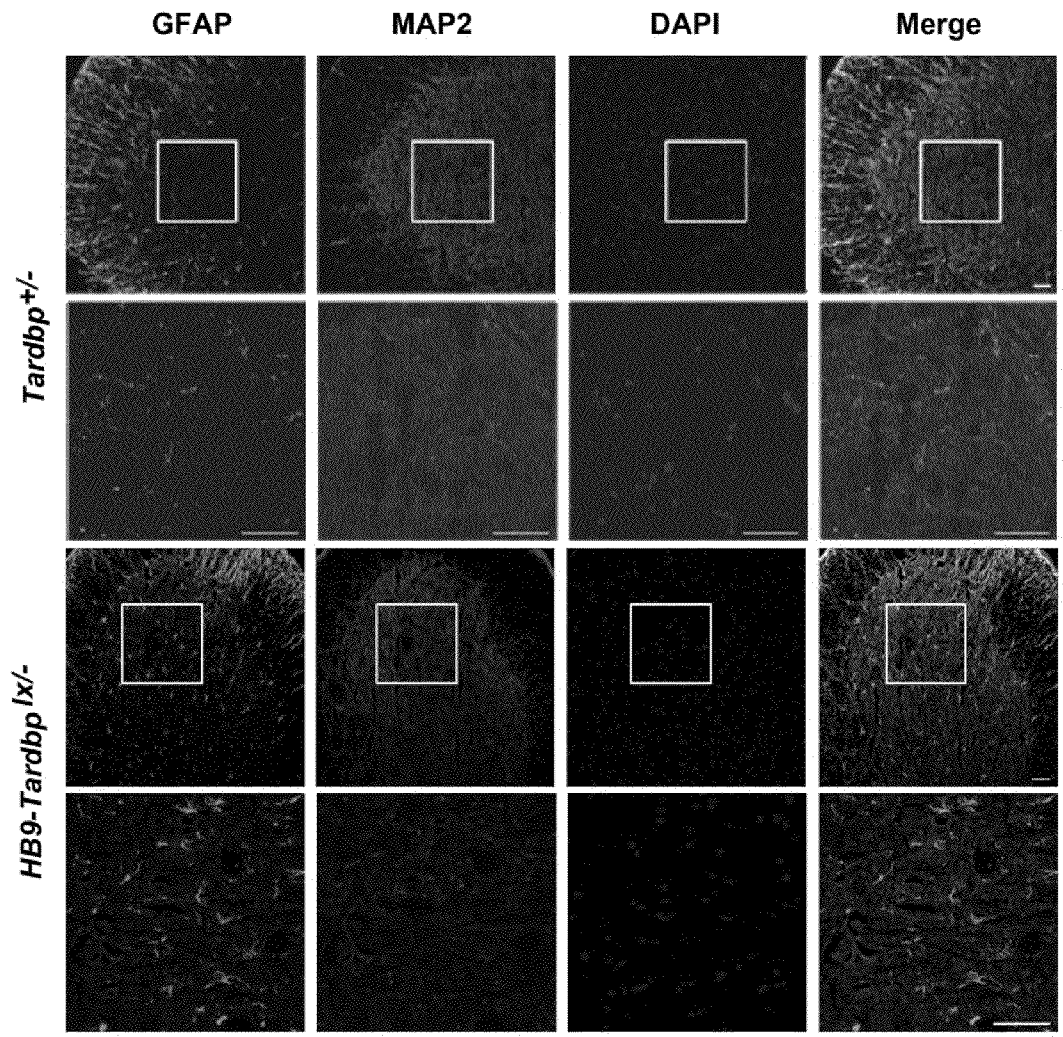
FIG. 4 shows reactive astrocytosis in the spinal cords of the HB9-$Tardbp^{1\times/-}$ mice. Multiple sections of ventral spinal cords from 20 week-old HB9-$Tardbp^{1\times/-}$ mice and control littermates were immunofluorescence-stained with anti-GFAP and anti-MAP2, a marker of neurons. The patterns of one representative section each from the two groups of mice are shown. DAPI staining indicated the locations of the nuclei. Note the enhanced level of anti-GFAP fluorescence in the mutant mice (lower panels) when compared to the control mice (upper panels). N=4 for each group. The scale bar is 50 µm.

The number of the motor neuron was further quantified by Nissl staining of the ventral horn of the lumbar (L3-L5) level of the spinal cords of mice. As seen in FIGS. 3B and 3D, the number of the motor neurons, which were characterized by their relative large areas, in the multiple sections of the lumbar regions of the HB9-Tardbp1x/− mice was decreased significantly. Since reactive astrocytosis was often taken as an indication of neuronal toxicity or neuronal death, the level of the glial fibrillary acidic protein (GFAP) expression was also quantified by immunofluorescence staining. FIG. 4 shows enhanced GFAP immunoreactivity was detected in sections of the lateroventral lumbar spinal cords of the HB9-Tardbp1x/− mice when compared to the controls.

One hall mark of the diseased cells of TDP-43 proteinopathies was the accumulation of poly-ubiquitinated proteins, including TDP-43 itself, in the cytoplasm. To see if poly-ubiquitinated proteins would also accumulate, in the absence of TDP-43, in the spinal cord motor neurons of HB9-Tardbp1x/mice, we carried out immunofluorescence staining experiment. As shown in FIG. 5, strong anti-ubiquitin signals were observed in the lumbar spinal cord cells of the HB9-Tardbp1x/− mice (lower 4 rows of panels, FIG. 5), but not in those of the control mice (upper two rows, FIG. 5). Furthermore, the cytoplasmic ubiquitin-positive deposits were mostly detected in the ChAT-positive motor neurons (lower four rows of panels, FIG. 5), suggesting the accumulation of poly-ubiquitinated proteins in these cells. The data of FIGS. 3-5 altogether indicated that the spinal cords, in particular the ventral horn of the lumbar spinal cord, of the mutant mice underwent significant motor neuron loss, reactive astrocytosis, and accumulation of poly-ubiquitinated proteins, all of which were characteristic of ALS with TDP-43 (+) UBIs.

Loss-of-Function of TDP-43 and Pathogenesis of ALS

The conditional TDP-43 knockout mouse model generated here is not the only one with motor neuron dysfunction and/or other pathogenic characteristics of ALS. As mentioned in the Introduction section, several genetically engineered mouse lines have been established for the studies of ALS, in particular that with over-expression of transgenic mutant human hSOD1. Since 90% of the non-SOD1, non-FUS-inclusion type ALS patients are signatured with TDP-43(+) UBIs, the ALS mouse model we have generated, though not expressing TDP-43 in the spinal cord motor neurons, should be valuable for research of ALS with TDP-43 proteinopathies.

Like other neurodegenerative diseases with inclusion formation during pathogenesis, e.g., AD, HD, Parkinson disease, etc., neurodegeneration in patients with the TDP-43(+) UBIs has also been suggested to be the result of loss-of-functions of TDP-43, cytotoxicity of the TDP-43(+) UBIs per se, or a combination of both. In vivo evidence supporting the first scenario includes the observations of depletion of the nuclear TDP-43 in diseased cells of ALS and FTLD-U patients with TDP-43(+) UBIs and the loss of motor function or learning ability of Drosophila with knockdown of TDP-43. On the other hand, current evidence supporting the second scenario is mainly by association, which includes the cytotoxicity observed in cell cultures upon over-expression of the carboxyl terminal 25K fragment to form cytoplasmic TDP-43(+) UBIs (36) and development of FTLD-U-like symptoms or motor-neuron degeneration in transgenic mice with over-expression of TDP-43 accompanied with formation of TDP-43 (+) UBI in vivo. With respective to the above, the effects of the restricted knockout of TDP-43 expression in the spinal cord motor neurons of HB9-Tardbp1x/− mice on the development of a range of ALS-like phenotypes in these mice not only demonstrates an essential role of TDP-43 in the functioning of the mammalian spinal cord motor neurons, but it also provides a direct evidence that loss-of-functions of TDP-43 is sufficient and thus could be one major cause for the pathogenesis of ALS with TDP-43(+) UBIs.

The molecular and cellular basis of how loss-of-function of TDP-43 would lead to the development of TDP-43 proteinopathies is currently unknown and may take a while to be fully understood in view of the multi-function nature of TDP-43. It is interesting to note, however, that accumulation of ubiquitinated proteins could still occur in the spinal cord motor neurons of HB9-Tardbp1x/− mice (FIG. 5). This suggests that accumulation of poly-ubiquitinated proteins in the diseased cells of TDP-43 proteinopathies is independent of the formation of TDP-43 (+) UBIs. We thus speculate that the initial loss-of-function of TDP-43, as the result of mutations of the ALS disease genes, may cause the impairment of the proteasome system and/or autophagy thus leading to the accumulation of poly-ubiquitinated proteins in the diseased cells. In the presence of TDP-43, these poly-ubiquitinated proteins then could form the TDP-43 (+) UBIs with TDP-43. This proposed scenario awaits to be validated in the future.

The TDP-43 cDNA (SEQ ID NO: 1) was cloned from mouse brain and sequences were the same as that disclosed in the NCBI GeneBank NM_145556. The primers a, b and c nucleotide sequences are 5'-TTCTGATGTCGGTGT-TCGTGC-3' (SEQ ID NO: 3), 5'-TGGCAACAGTGTTAC-CATGTGG-3' (SEQ ID NO: 4) and 5'-CTCAACTTTC-CTAAGCTGCAATCC-3' (SEQ ID NO: 5), respectively. The sequence of Cre recombinase is listed as SEQ ID NO: 6 and HB9 promoter as SEQ ID NO: 7.

In summary, ALS, or amyotrophic lateral sclerosis, is a progressive and fatal motor neuron disease with no effective medicine. Importantly, the majority of the ALS cases are characterized with TDP-43-positive, ubiquitin-positive inclusions (UBIs) in the cytosol or, to a much less extent, the nuclei of their diseased cells. By using the conditional mouse gene targeting approach to investigate the functional roles of TDP-43 in the spinal cord motor neurons, it was discovered that mice with inactivation of the Tardbp gene in the spinal cord motor neurons (HB9-Tardbp1x/−) exhibit progressive and male-dominant development of ALS-related phenotypes including kyphosis, motor dysfunctions, muscle weakness/atrophy, neuron loss, and astrocytosis in the spinal cord. Interestingly, immunofluorescence staining experiment suggests the accumulation of ubiquitinated proteins in the motor neurons of the spinal cords of HB9-Tardbp1x/− mice with the ALS phenotypes. The discovery not only establishes an important role of TDP-43 in the functions of the mammalian spinal cord motor neurons, but it also suggests that loss-of- TDP-43 function is one major cause for neurodegeneration in ALS with TDP-43 proteinopathies.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A conditional TDP-43 gene-knockout mouse model for amyotrophic lateral sclerosis (ALS) whose spinal cord motor neurons comprises a disrupted TDP-43 encoding gene and have a loss of TAR-DNA binding protein-43 (TDP-43) function, wherein the TDP-43-encoding gene in the spinal cord motor neurons comprises a homozygous disruption and the mouse exhibits ALS-like symptoms after the age of 13 weeks.

2. The conditional TDP-43 gene-knockout mouse model of claim 1, wherein the mouse does not express TDP-43 protein in the spinal cord motor neurons.

3. The conditional TDP-43 gene-knockout mouse model of claim 2, wherein the mouse expresses TDP-43 protein in the cells other than the spinal cord motor neurons.

4. The conditional TDP-43 gene-knockout mouse model of claim 1, wherein the TDP-43-encoding gene in the spinal cord motor neurons is inactivated.

5. The conditional TDP-43 gene-knockout mouse model of claim 1, wherein the TDP-43-encoding gene in the spinal cord motor neurons is inactivated and/or deleted.

6. The conditional TDP-43 gene-knockout mouse model of claim 1, wherein the ALS-like symptoms is male dominant.

7. The conditional TDP-43 gene-knockout mouse model of claim 1, wherein the mouse expresses Cre recombinase in the spinal cord motor neurons, but not in other cells.

8. The conditional TDP-43 gene-knockout mouse model of claim 7, wherein the Cre recombinase is driven by HB9 promoter.

9. The conditional TDP-43 gene-knockout mouse model of claim 8, wherein the mouse comprises Lox P sites in its genome, and the cells other than the spinal cord motor neurons in the mouse comprise a TDP-43-encoding gene with a pair of Lox P sites.

10. The conditional TDP-43 gene-knockout mouse model of claim 1, wherein the mouse exhibits an inflection point in its body weight curve at about 13 weeks.

11. The conditional TDP-43 gene-knockout mouse model of claim 1, wherein the mouse exhibits one or more of the following phenotypes:
    (a) kyphosis;
    (b) abnormal hind limb clasping;
    (c) deficiency in motor coordination;
    (d) motor neuron loss in the spinal cord;
    (e) astrocytosis in the spinal cord;
    (f) a weight loss as compared with a control mouse; and
    (g) accumulation of poly-ubiquitinated proteins in the spinal cord motor neurons.

12. The conditional TDP-43 gene-knockout mouse model of claim 1, wherein the exon 2 and exon 3 of TDP-43-encoding gene in the mouse spinal cord motor neurons are deleted.

13. A tissue or a motor neuron which is isolated from the spinal cord of the conditional TDP-43 gene-knockout mouse model of claim 1.

14. The motor neuron of claim 13, comprising ubiquitinated protein aggregates and having no TDP-43 protein expression.

15. A method for identifying an agent with potential for treatment of a disease associated with a loss of TAR-DNA binding protein-43 (TDP-43) function in an animal, comprising:
    administering the agent to the conditional TDP-43 gene-knockout mouse model of claim 1; and
    determining whether the agent prevents and/or inhibits at least one of the ALS-like symptoms;
wherein prevention and/or inhibition of the at least one of the ALS-like symptoms is indicative of an agent with potential for treatment of a disease associated with a loss of TDP-43 function.

16. The method of claim 15, wherein the exon 2 and exon 3 of the TDP-43-encoding gene in the mouse spinal cord motor neurons are deleted.

17. A method for identifying a candidate agent for treating, preventing and/or inhibiting ALS associated with a loss-of-function of TDP-43, comprising:
    administering the agent to the conditional TDP-43 gene-knockout mouse model of claim 1; and
    determining whether the agent prevents and/or inhibits at least one of the ALS-like symptoms;
wherein prevention and/or inhibition of the at least one of the ALS-like symptoms is indicative of a candidate agent for treating, preventing and/or inhibiting ALS associated with a loss-of-function of TDP-43.

18. The conditional TDP-43 gene-knockout mouse model of claim 1, wherein the mouse exhibits one or more of the following phenotypes:
    (a) kyphosis;
    (b) abnormal hind limb clasping;
    (c) deficiency in motor coordination;
    (d) a weight loss as compared with a control mouse.

19. The conditional TDP-43 gene-knockout mouse model of claim 2, wherein the mouse spinal cord motor neurons comprise ubiquitinated protein aggregates.

20. The conditional TDP-43 gene-knockout mouse model of claim 1, wherein the mouse exhibits a loss of spinal cord motor neurons.

* * * * *

SEQUENCE LISTING

```
<160> NUMBER OF SEQ ID NOS: 7

<210> SEQ ID NO 1
<211> LENGTH: 414
<212> TYPE: PRT
<213> ORGANISM: Mus musculus

<400> SEQUENCE: 1

Met Ser Glu Tyr Ile Arg Val Thr Glu Asp Glu Asn Asp Glu Pro Ile
1               5                   10                  15

Glu Ile Pro Ser Glu Asp Asp Gly Thr Val Leu Leu Ser Thr Val Thr
            20                  25                  30

Ala Gln Phe Pro Gly Ala Cys Gly Leu Arg Tyr Arg Asn Pro Val Ser
        35                  40                  45

Gln Cys Met Arg Gly Val Arg Leu Val Glu Gly Ile Leu His Ala Pro
    50                  55                  60

Asp Ala Gly Trp Gly Asn Leu Val Tyr Val Val Asn Tyr Pro Lys Asp
65                  70                  75                  80

Asn Lys Arg Lys Met Asp Glu Thr Asp Ala Ser Ser Ala Val Lys Val
                85                  90                  95

Lys Arg Ala Val Gln Lys Thr Ser Asp Leu Ile Val Leu Gly Leu Pro
            100                 105                 110

Trp Lys Thr Thr Glu Gln Asp Leu Lys Asp Tyr Phe Ser Thr Phe Gly
        115                 120                 125

Glu Val Leu Met Val Gln Val Lys Lys Asp Leu Lys Thr Gly His Ser
    130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

Leu Pro Asn Ser Lys Gln Ser Pro Asp Glu Pro Leu Arg Ser Arg Lys
            180                 185                 190

Val Phe Val Gly Arg Cys Thr Glu Asp Met Thr Ala Glu Glu Leu Gln
        195                 200                 205

Gln Phe Phe Cys Gln Tyr Gly Glu Val Val Asp Val Phe Ile Pro Lys
    210                 215                 220

Pro Phe Arg Ala Phe Ala Phe Val Thr Phe Ala Asp Asp Lys Val Ala
225                 230                 235                 240

Gln Ser Leu Cys Gly Glu Asp Leu Ile Ile Lys Gly Ile Ser Val His
                245                 250                 255

Ile Ser Asn Ala Glu Pro Lys His Asn Ser Asn Arg Gln Leu Glu Arg
```

```
                260                 265                 270
Ser Gly Arg Phe Gly Gly Asn Pro Gly Gly Phe Gly Asn Gln Gly Gly
            275                 280                 285

Phe Gly Asn Ser Arg Gly Gly Gly Ala Gly Leu Gly Asn Asn Gln Gly
            290                 295                 300

Gly Asn Met Gly Gly Gly Met Asn Phe Gly Ala Phe Ser Ile Asn Pro
305                 310                 315                 320

Ala Met Met Ala Ala Ala Gln Ala Ala Leu Gln Ser Ser Trp Gly Met
            325                 330                 335

Met Gly Met Leu Ala Ser Gln Gln Asn Gln Ser Gly Pro Ser Gly Asn
            340                 345                 350

Asn Gln Ser Gln Gly Ser Met Gln Arg Glu Pro Asn Gln Ala Phe Gly
            355                 360                 365

Ser Gly Asn Asn Ser Tyr Ser Gly Ser Asn Ser Gly Ala Pro Leu Gly
            370                 375                 380

Trp Gly Ser Ala Ser Asn Ala Gly Ser Gly Ser Gly Phe Asn Gly Gly
385                 390                 395                 400

Phe Gly Ser Ser Met Asp Ser Lys Ser Ser Gly Trp Gly Met
            405                 410

<210> SEQ ID NO 2
<211> LENGTH: 34
<212> TYPE: DNA
<213> ORGANISM: Bacteriophage P1

<400> SEQUENCE: 2
ataacttcgt atagcataca ttatacgaag ttat                              34

<210> SEQ ID NO 3
<211> LENGTH: 21
<212> TYPE: DNA
<213> ORGANISM: Artificial Sequence
<220> FEATURE:
<223> OTHER INFORMATION: primer a

<400> SEQUENCE: 3
ttctgatgtc ggtgttcgtg c                                           21

<210> SEQ ID NO 4
<211> LENGTH: 22
<212> TYPE: DNA
<213> ORGANISM: Artificial Sequence
<220> FEATURE:
<223> OTHER INFORMATION: Primer b

<400> SEQUENCE: 4
tggcaacagt gttaccatgt gg                                          22

<210> SEQ ID NO 5
<211> LENGTH: 24
<212> TYPE: DNA
<213> ORGANISM: Artificial Sequence
<220> FEATURE:
<223> OTHER INFORMATION: Primer c

<400> SEQUENCE: 5
ctcaactttc ctaagctgca atcc                                        24

<210> SEQ ID NO 6
<211> LENGTH: 1053
<212> TYPE: DNA
<213> ORGANISM: Bacteriophage P1
```

<400> SEQUENCE: 6

```
atgcccaaga agaagaggaa ggtgtccaat ttactgaccg tacaccaaaa tttgcctgca        60
ttaccggtcg atgcaacgag tgatgaggtt cgcaagaacc tgatggacat gttcagggat       120
cgccaggcgt tttctgagca tacctggaaa atgcttctgt ccgtttgccg gtcgtgggcg       180
gcatggtgca agttgaataa ccggaaatgg tttcccgcag aacctgaaga tgttcgcgat       240
tatcttctat atcttcaggc gcgcggtctg gcagtaaaaa ctatccagca acatttgggc       300
cagctaaaca tgcttcatcg tcggtccggg ctgccacgac caagtgacag caatgctgtt       360
tcactggtta tgcggcggat ccgaaaagaa aacgttgatg ccggtgaacg tgcaaaacag       420
gctctagcgt tcgaacgcac tgatttcgac caggttcgtt cactcatgga aaatagcgat       480
cgctgccagg atatacgtaa tctggcattt ctggggattg cttataacac cctgttacgt       540
atagccgaaa ttgccaggat cagggttaaa gatatctcac gtactgacgg tgggagaatg       600
ttaatccata ttggcagaac gaaaacgctg ttagcaccg caggtgtaga aaggcacttt        660
agcctggggg taactaaaact ggtcgagcga tggatttccg tctctggtgt agctgatgat      720
ccgaataact acctgttttg ccgggtcaga aaaaatggtg ttgccgcgcc atctgccacc       780
agccagctat caactcgcgc cctggaaggg attttttgaag caactcatcg attgatttac      840
ggcgctaagg atgactctgg tcagagatac ctggcctggt ctggacacag tgcccgtgtc       900
ggagccgcgc gagatatggc ccgcgctgga gtttcaatac cggagatcat gcaagctggt       960
ggctggacca atgtaaatat tgtcatgaac tatatccgta acctggatag tgaaacaggg      1020
gcaatggtgc gcctgctgga agatggcgat tag                                    1053
```

<210> SEQ ID NO 7
<211> LENGTH: 15210
<212> TYPE: DNA
<213> ORGANISM: Mus musculus

<400> SEQUENCE: 7

```
tttatttac attccatctc caccctgggg gatgggaaag ctaaataata atttagcatg         60
cataagtaga catttcttc tttatatata aatacaatat acaaaaatac actaccattc       120
tgagattttt ttcagcaatc tgaatgctca tgacataaca cctcactcca ctaccgcccc       180
ccccccatac ataggcataa cacctttttc ctccctctgt tttaaatttt cagcagaatg       240
gttgtctcca aaggagggtt caagtttcta ggtcacttaa cactgttttt tcctttctcc       300
gacgaaggaa gagtcaggca ggagccactc ctagaaaggg taggttctcc cagataccctc      360
tggccaacat cacccgaaat taatgtata agaacgaaaa gctcacattg gagctcctct        420
ctcattctct cttgctgtcc cctcgaggtc ccaaaaagga tccgcagccc agcctgcact       480
tggatgcatg gttcggggag aggctgtcag cctggctgca ggccatagga tgggattgta       540
aactccccca gccccgcag ccccccaggt agccatcttt cgcatccctg cttccgccct        600
ggaggcaact actggggcag aggttggtgt ccaggcccgc ctagtcttgg aggaggcgag       660
tcgtcctcag atgagcagtc ggatgaggca gcatgggcac cggcaccatt gctgtacggg       720
aagttgtcct cttcttcatc atcctcgtcc tcatcagggt cactgtcccg caagtcccgc       780
aggcgacggc gcttgccttt gtcccccgaa accggaggcc ccatcagctc ctcttccgtc       840
ttctcctcac tgccgccttt gccggtgccc ccgccgccgc ccttctgctt ctccgcctcc       900
tgcgcagcct gctcttgggc cttttttgctg cgtttccatt tcattcggcg gttctggaac      960
caaatcttca cctgcaggca taatctggcg tgagaaactg gccacccgca tccccacgaa      1020
```

-continued

```
tccagagggt gagagcgtac aagcattcgg gacccctgct ccttggccta ccctcgccct    1080
agaagaggtt tcgctagagg actaagactg actggcagcg gcgtctccac gtcttcgccc    1140
cttaaatcta ctctatttaa caataacgcc atgggtgtag tgtccctaac tccccaactg    1200
ggcgcgtttt aataccctcg gtctaccgag gcaccaaggc agctcgcaat gtcaccaaac    1260
tctcaagtct gcacctttct agaaaaataa cttctttgaa tgtggccgga gggcacactc    1320
cagaatagct tgttaaatac agattctcag cctgctcccc aacttaactg aatcaaacct    1380
ccagagcatc ctagaacctc acgctgaaaa tcaatcccca acgtaaagat aaagaaacta    1440
gggctcagtg tcccaaatca gcacccgcct tcagggtggt cgggcgcgcg cgcacctgag    1500
tctcggtgag catgagcgag gtagccacct caaaacgctt gggtcgagac aggtacttgt    1560
tgagcttgaa ctggtgttcc agctccaaca gctgctggct ggtgaaggcc gtgcgaggcc    1620
ttcggcactt ccccaagagg ttcgactgcg cctgggctgg ggacagaaag gcaagaggc    1680 ttctgtaaat ttgtccactg agggcgaggt agtgttccac ccgtcgctgc ccttttcct    1740 cccgtgatcc aacctccaga gcccacccct cagacgcttc agcctcagtg cccactccct    1800
atggcccaca tctcagacat gaagtggaag tggcgagctc atctcatttg agaaaaaagg    1860
gcctgttgcc tccgctcagt ggccacccga atgaacagga ggagggttgg tctaaaggct    1920
tgggtagcta aactggacta gcaagcatag agaccaggtc gctcccattc tcatggaagg    1980
cttctctcca cctcaagctg gaaaagaacc catcctcttg gttccaccac gatcttaaag    2040
cagaagagac aggggcgtg ggcgcaggaa cggtgggggga gggagaaaag gaaggatagg    2100
gactgaagct agagtctaaa taggcattca tctgcgtgtc ttcacgtctc tgttgacaaa    2160
ctctcccctc ctagtgctaa ggccaaaggc tgaggactgg aagcctattg ggacgattct    2220
cattactcaa attaaaggtt gagctgtgag tagatctggc tttctgtgtg ttccgggaga    2280
tctgtccagc tttatttaca taatttcgca cagttacatc acagagaatt ttatgacctc    2340
aaaatgaaac ttcccttgat ttcccaggag tgcgaaaagt gttagacaat aaaagaaaga    2400
aagcaaggga aagaaagagg ccagcccctg gctgggatga gctcaggctc ccctgggatg    2460
ggtaatttgc tttataggaa ggtccacgcc ccctgcttta gttaaacaag gctacaaatt    2520
cccagcttga caatacatta gaactctaat taaaacgctg tcttggaagg gatcatttgg    2580
gaaatgccat ccagtagaaa caaccaatta aagaaaacca agctagtttt cccaggggag    2640
agggaagtcc caggaacaga acatattcag ccacccctccg ctgcattcct tagtgtccat    2700
tgggatctgg ggcttggctt tcttttccta atgtagacct ggccatactt taaatgccca    2760
caccatgaga catcatgggc tggatattct ggcaaaggga tcccacttac atggattttg    2820
attgatcctg ggctccacaa aaacatccct tttctcccag agaccacttg tgtagccagt    2880
aaacccagag ctatggaggc ctgttgttga ccactggtca gctcttctca ggaccactat    2940
gcttctcagg cctggaaagt ccagccatag tggacatctg aaacctgggt tcctcagcca    3000
ggcacagatc ctgcctagga cttagtgaat aggaatgatt tcagagatgt ctgagctgca    3060
gtccaactga ggttaaaggg agccttcct ctttgctgag atcaacaagg ctagtcttct    3120
tggagccaag ctgggaaaaa cctgggtggc tgcgagcaaa caagtgcgca ggctgtgatt    3180
ctctcaccac cttgctactt ctgcggttct ctggggcccc agctttctct gtttagtcat    3240
gaccaccgct tccagcagag gaatctgaat tctggcaaat gtttattct gttttctttt    3300 ttgctttttt tctccctcca gtgcctgcat cttcccagtc taaacaaacc cactcagacg    3360
gaaacaatgg ggtctctttg tttgggtgtt gagtggctga caggagaaag ccatatacat    3420
```

```
cttctggtcc atccattcag gaaaggcagc ttgcccctat ccaagtcagg cacagagcag   3480
aaatcagagc cagggtgccc tacacagacg ctgcatgtgc cagggaagtc ggaaatgtcc   3540
cccctcccgc aaggttgtcc ctattgggta acagagagga tgcagaagac tggacctttg   3600
tgccctcacc ttggacagga actccccaag gtgttgagca cctgaagttc ccagccaggc   3660
actttctatt tatagacccg gtgacccttat attcaaacag accagttcga catcatttgg   3720
agggacgccc accctcacca acacacacac acacacacac acacacacac acacacacag   3780
agagagagag agagacagag acagagacag agacagagac agacagagac agacagagag   3840
acagagacat gcaaatgtct tgcccttcaa aggaaggcag agtccttaca agggccacgg   3900
aagagctact tctggaccca gtgatgtgtc tcttcatagc ctataatgga acctctgaca   3960
aagttcattt tctcaagata agtccccggt ttcagcgacc cccaaaacct gccctaatcg   4020
aggctagcct ttccgcgcac ttccttgtcc agcttgcagg ttattcttta ggttttagcc   4080
tcacacctcc aacctcccct gtctgttaag agagatagag aggccaaggc ctgcttgtgg   4140
ccatcttaat aatttgaggc tcctttcatt ctgtgcggcc cacgagaggc ctcacaggcc   4200
caggaatgag ccacagaggc ttcgatgctc ttccacagct cgctaggagg tgagagcaaa   4260
aggaaggggg tgcgagagag gaggatgcgc gtgagaactg tccgggtgcg gcgcaggtac   4320
tcacagctga agtccggcat cttgggcagg atcatgcccg cagtagacgc gcgcagccac   4380
tggtccagtt ggaaggtgct ggcacccagc ttgatggggt cggcagggtg cgcagggtgc   4440
gcgccctgca cctgagggta tgagtaggaa gcgccgggt gctggccagc tagcgcggcc   4500
gctgcagctg ctgccgaata actgtagacc gggtgtccat agagagccgc ctgtgcaggg   4560
aggcccgcgc cgccctgtgc gcccccgggg tgcagcccca gtgccaggcc accggcagcc   4620
gcggcagcgg cagcggcagc cgcggcggct gctgcaccag ggtgcgcgtg tggtgggga   4680 gtgcccggcc caccgccgc gccgccgcct cctccgcgc ccaggaatcc gggcttgggc   4740
agcagcgcgc agtgtgcagc cagcaagcgt gggggcgacg ggctctcagc tctcagccgg   4800
tcaccgggcg ctgcagtggc ctccgaggat gcgggactgc agctacggct cgccccgcta   4860
ctggtccccc cgccgccgct gccgccgcgg ccgggaccag atactgtagt cgcgagggaa   4920
gtgaccaagg ccagaggcgc gctctgcgtg gaggcggctc gcgggggatc cacgccagc   4980 agggcgtcga tgcggaaatt tttggatttt tccatcggct cgattggagc tgacaatcag   5040
ggtccaaggg tgggcgatgc agtcgtgtgc gggcttacgg agactgagcg tggcggtggc   5100
cagccttggg gccggtattg ttactgcgat tttttgccaa taaagtcgca gccggaaact   5160
cagctgagag cgaccatcgt ccaggcgcct cctctttgcg gtcctcgtgg gaccgcgct   5220 ccactcactg gtatgaactt ccaccggagc gctcctgcga gtttgtgttg gggagaccgg   5280
ctctctgctc tcaagagctc aagcgaccgc atcgaggcca ctggtgcctt ggtggggacc   5340
cgcgcccctc cgcacacttg aagctcaggg cggtctggga ttggcgcgct cagcgggggc   5400
ccgaggaggg ctgtctgccc ggcgattggc cgagggctc acctgtcacg gtccaattag   5460
cctgacgccc cgccctgcg ccccaggtc ctaagcagcc ggtggtgaac agcgtaggtg   5520
gccggaggag gcaggttgga gagtttggag gctgaacaca agcttactgc ttccttgctg   5580
ctgggagagt ggtgagcgcc agtaaccctg ggtcccagtg agtgccccc gagtcccttt   5640 gacaccttgt tcctccagag gcggacgcct tatcttcctc cagctactcg cgctcccttg   5700
agggagttgg ggaatgttct gcactgagga actaggtggg tcctcacccc tgaagtccac   5760
taggtaccca aaacgggacc ctgagcttag tacactgaag actgttcggt ttcccaaaat   5820
```

```
ctctcgcgtt cctgagtgtt gattgcttca agatggtttg cgtccctgtc attaaccctc    5880
agcaggtcga accttcttat ctgcccctcc cccaaaagta tcatgcgccg caaatgtttg    5940
tttgtagggt ttcggtgtgt ataaatacgg tattagaggt tgaagcctac aaatcttcag    6000
tcagagtgga gagagagcag ttttccaact cagagatgca cattgacttg aaggtcgttt    6060
gcacaggtgc cactgagccg gacctaggtg agaaccaagt tctattagag ccttgccttg    6120
tgggggtgta ggaaaaaggc tttgcgggaa ttggccgagg actgctccct cggactgagc    6180
cagttcgcag gctaagggag ccactatcag gctctcgcct cctcctgccg gccgagttca    6240
ggaaaatcaa gaaagggctt ccagagaccg tattaaagtg tgaatccaga cctcagcctg    6300
cgcacatatc aaatatttac tgtaaacacg cttccggggg cttttttttt ttaatgtaac    6360
gaatcaataa gtagtttgag aaatcaagct ttctcgctag ctccattctc gggtatcttc    6420
cccaaacacg aggggaaagt gggagggagt tccaggtctc tggatcgcgg cttcccaacc    6480
aggtgagagg ttaataaaag atcggaaatg cccagggaa ggccaggagg ctaggacaat    6540
ccttgttggg tgaatttaaa agtagcaggc aaagctgttt caagagggat tgggggtggg    6600
gggtaacgat aaatataagt aaggactata ttttccctgt caacaagttt tgtttaggag    6660
agatttaacg cagtgattct gttgggatga gtgagtaggt ttttgttttt tgttgttttt    6720
gttttgtttt tgttttgat tttggagaca gggtttctct gtctagccct ggctgtcttg    6780
gaactcactc tgtagaccag gctggcctcg aactcagaaa tcctcctgcc tctgcctccc    6840
aagtgctggg attaaaggtg tgcgccacca tgctcggctg agtggagttt ttattatgac    6900
agggtggtcc tggctggaaa atctggaacc cagcggggaa catcttggag taagttgtgc    6960
acagctttgc aaaggcctcc agctagtctg aaaatagtac aagcacatag ctcttgtctt    7020
taggtgctgt ctcttgggg tgatgaaaat gcagctctgc cttttagagg gttaaaggaa    7080
cacttgtgtt ccatgagtgg ttccctgcca gttctcctat cttggaagcc caattaaggc    7140
aagtaaggat gctgggatgc cctacccca tccccaggat tcagtcttga ccccattgca    7200
tttacagaaa cttgtgttta aggcccatgg gccttttcca gatgagagtc ccaaagaaga    7260
aagagaacct aaccatggtg aggcaagtct ctaatcccag cactcaggag gcagaggcag    7320
gtggggtctg tgagttctag gccagcctag tctacagagc cagttccagg acagcaacca    7380
aaaatgctac acagagatac cctgtcttga aaaaacaac aacaaaacaa acaaaggaga    7440
agaaggagga aaaaagggt ggctgcagat gagattttcc tggggtggac tcatgggacc    7500
cgaatcatct ctaaactaca caaccagggt tgttttggt gatgatacag tattaggtct    7560
actgagttta ggcacaggtt tccttagtaa agtcatccga gaagaggaat tcatttcctg    7620
tttgttgtgt aggggatgtg atccaaaagc ttctaaatcc ctttcaaacc cttcccactt    7680
cgtctggtgt ttgaccatcc accaggctaa cccacaccag tccccaccac ctgtgggctg    7740
agtgaggttg tatcaagagc cccttcagcg aagggaaat ttgcatatca gacttgatgg    7800
atatatttct ttgtttgaca aagtgggggt tgggccaaaa agactctgaa gtcaaagggc    7860
ttgaatatga tcatatattc tgcttcggtt tgagcggaaa cttgtatcct gagaggtggg    7920
agttgggaga gagactggga gtcgtctgga actgggatct ttgtgtgttt tacgagtgga    7980
gtgagcatgc tgcgtctctt cctgttccca gcgtctattg acccagccca gctggctctg    8040
gggcagcctg ggactgagct gggggtttac tacggtaccc ttgagagatc aaaggtctgg    8100
tcccagaagc atgcctattc tttttttttt tttattaga tattttcttt atttacattt    8160
caaatgttat ccccctttcct agtttcccct ccccaaatcc cctatcccct ctcccctccc    8220
```

```
tctgctcccc aacccacctg ttcccattcc tggtcctggc aaaaaaaaat aaggaatgct   8280
tcacaaattt gcatgtcatc cttgcgcagg ggccatgcta atcttctctg tatcggttca   8340
gttttagtat aggtgctgcc gaagtgagca cagcattccc attgttgtgc ctcaaggtag   8400
ctcccttctc cagaagcccc aggggccaaa tgaggctctt ggagggcaga gaggaagacc   8460
tctcctaccc aaaagaggct ggaatttaag gcccggtgta catttaatca tctggctccc   8520
agtcattttt ttctctgcgt ctagccagga tccctctttt gggtcttgca ttaagttact   8580
gaatataact tgtgattgag cctcctctca ttactgagaa aggtgtgttg atttatacaa   8640
ataaccacaa ggaaataaga tgttggggtg gggagtatag tggttccaca gttcagtgct   8700
taagagtgag tgcagctctt gaggaggacc caagttgggt tcccaccact cacactcaca   8760
accacctcca actccagcta caggaaatcg gattccctct tatggcctct ttgggtacgt   8820
gcattcccat aaatagacac aaacatacac acaatgcaaa cataaaaaga aaacttacaa   8880
agatgttata atctacaagt tttacccctg acattataca agaactcaga acaaaaccta   8940
catgcaccca tattcacagg tcaggtcagc attgattcta taactgatca cctacaaaca   9000
catccctttc tgtggaatgc agcaggtaca atatataata gccattaaca aaaaggccaa   9060
gagcctggag gtatggctag gagactggat ggaaggcagc attccctgca tctccctcca   9120
cacacctgcc atttgtctgg ctgtttccaa aacttaaaac aagcaacccc ctgcccacag   9180
cagcctcatg gagaaaggtt catgaagact gacttctcag cccttttgaa ctccatgaga   9240
gttaactcac atcaacattt tgaggcgggg ctggtgagat ggctcagtgg gttagagcac   9300
cctactgctc ttccgaaggt ccagagttca atcccagca accacatggt ggctcacaac   9360
catctgtaac gagatctgac tccctcttct ggtgtgtctg aagacagcta caatgtactt   9420
acatataata aataaataaa tctttaaaaa aaaaaacatt ttaaggcttc ccttcaggaa   9480
aatgagcctg gaggatgtag tgaggccagt gaggtccagg acacaagccc acaggggtgg   9540
tgatggtggt atttttcaga ggctgaataa gtactcagga ggacagaaag caagcaggaa   9600
gtgtgaatgc tggacctgga aggtcataga ccaacttcct tcaagtcaga ctgaaatcag   9660
tgcttggaat gtctctgggg acataacccg tccacccacc ccagcctgag gacacacaga   9720
atccaatggg gagcctgggg tcacaggag gtgagatcag gagaagggat gtctgatgag   9780
tcccccccca cacacacaca ctcattacag ccccttcaga gcccaaaagt accatcagct   9840
cctttattac catcctttga tctaccaccc ttttctcaga cctccatccc cagttcagct   9900
ttaaaggggt ggtttgcaaa ggtggctcag aagacaggtg acctgaagac ccagtgttcc   9960
aacctgaggt gaactgctct tgccaaggac actacaagcc agtccttttc tttgccagcc  10020
cccccccctt ctctacctct cccagcacac ttggatttcc ttcctcccct tttagaaagc  10080
ttactctgcc ctccctactg cctggtccac cctcaggcca tcttcactgg ctgcccttct  10140
ccactggccc cattcctcct tgtaaataaa taaataagtc cagcccaaac ctgggttgta  10200
ggggtacagg gagaaagaca gtaagatata aatttgaaaa actccagcac aaaaatatat  10260
tctatatttg aaaattttac tcaaggtttc gggttttttgt ttgttttgct gtgtacttag  10320
aacatagaga agagactgag ctcagccctg cgctggatgc tttctgaccc aggaagccaa  10380
agacattttc aatttctctt acaatcctag aggccatagg tatgaatcat aaagagaaac  10440
aaggctaaga gaggtcacct cagttctttt aatcagctag ggtgtgtgtg tgtgtgtgtg  10500
tgtgtgtgtg tgtgtgtgtg tgtgtgtaag taaaacagca ccctcagaag aaacgaaaga  10560
cttctcagga aacctgtact tttgctccaa gatcttactg caaattcatt gtataggagc  10620
```

```
ttcatatcat gggcaggaca aagaacagaa gcaagctcca agcaggctgt gcagccctct   10680
ccccacctcc actacccacc tgcagggctt ggtaagtcat ccacagaaag ggtctgcttt   10740
gaaggtgata acccagcttc ccatagctgg ggcgatgtac gtttaggaca caaagcctgg   10800
ctctgtaaag gctctggcta ctgttcttag ggcactccca caactttcta agtcacttgt   10860
ttgcccctga tcaagcagaa gaagattaca ctggcaatac tgaagcccca gaaacaaagt   10920
ttacaaccac cgggaaacaa tgcaattcat gttttaaaaa tataaaaaca aacaaaaagc   10980
gacaaaaatt gtctgcctag cctggactcc accactgacc tatatgatgc tggtgtgcat   11040
caaacacgaa gggaagaaac ccagttacac aaacacagac gttgtctggg aacattttaa   11100
tgcctcggtg agtgaatttt ttagtgtgtt ctgacttgaa attatggtga atcagggcgt   11160
actaatgccc aagtctacag cagataatgg caggaagtcc tggctaattg gtctattcac   11220
tcactacttg ctgaggtagc agaagctaac actacaggag gcagagtgag gacaaggagg   11280
aggggcgggg atgctgagct acctccagag cagcgcctca cagctgtggg gtgggggtgg   11340
ggggcgcgac gacaggtgag agttgggttc attttccagc acaggcatct aggatcaggc   11400
tcacctcaac ctgccaaagc ctcctaccac aggagtaagg gggcccgaag gacccaacag   11460
ggtcatgcca gaagctcttc ccagagttgc ttttcttagg gcagtgatct cacaaattgt   11520
ggaaggaaac acacctacct tctactctac agatggacgg acagaccaag gctccaagat   11580
gtccaggttc tttgcttaag aagcacagaa taaagttcca ggggctctga ctttgatttc   11640
tgcactaggt ttgttccaca atatgggtca gtgccctggt tgttagaatc tccgtgtttc   11700
ctaatcatta tgattccttc ccaccactcc accacctcgc tggtctggcg cataagtcac   11760
atcagagatg ccatctttgc ctttagtgtt cctaggcccc tttggggagg atgtcctttc   11820
tctttccttc ccacaactgt tcttgcagac tagcagggag ggagaaagac ccaccttctc   11880
ccctactctc cctacagtct ctggggtcct tgctgcaggc aagataattt ggctaatgaa   11940
ctcgttaaag ggcccctggt gacccgccct ggcctcccct tgggcccatct gggaaattcc   12000
actgaaaggc tgagagcgct ttgcagctcc gctgccgtct gtcactgcag gaggcctgaa   12060
gtagacccct tacattaaaa taattaccca aaggaacagg tggcccactc cctaagacca   12120
ggcgcatctg gctgagcctg gaagtgttgc gagaaaggcc cgcccagggc agggcaggtc   12180
aagctggagc ctgggagggc ggagaaggac cttcgcaggc ctgtggattt ctggacaccc   12240
gccaactggg cgaccaaagc cttgagagaa ggtggctgat tgcgccgcca cccaccatct   12300
ctgtatgctg gtgacagaac cgaaccttga gctctccgag gttgactcca aggttggtga   12360
gcgtccggca ttgggcttca gaccaggggc tcgcaggaga gagcaatgcc agcatccccg   12420
catgagaagg aaaggcagct caggtagtat gtcggagcat gtgtccacgt gcatgtgtgc   12480
actgagcgcg cactgagagc ctgggcgcaa gtgtgcatat gtgtgcaaag tgcctccttg   12540
ttcacgcgaa gagacatcgt agattgttga ggaagtcccc tgcagtgtgg ccgaaaggaa   12600
cagcgcgcgg ctccggcgag cggccaagcc tattgccaaa aacatgtatt acactgcgac   12660
attctgtaaa tgagataatg atacataaac ccgatgatcg atgtgacggg cctggatgtc   12720
ttctctaaat tagctgctca catcgactgc taatattgtg agtttatgaa agcaatttcg   12780
gtgcaatcgg cgagagggtc ttcttactct aatcagcctg cctagctaat ggaagagggg   12840
gtcaggctga gcgttattga cacgtccgtg cccttaaacc tgtttcccaa taaagctgat   12900
tagtttttgt caattcatca gctaaccact ctggctggaa acaaatcaaa gctgtatttg   12960
ttcaatagaa gcaacaagtc acagatcagc accattcagg gggagggctg gtcaggacct   13020
```

```
gccttaggga gaaatgtcca tgaggcatct ctgacctggg aaccttaaaa taagtataat   13080
aggtagaact gcgcctctag tcttccttcc ttcctttaat cagggctgca ggtggactgg   13140
atcccggact actctttccg atgtggaaag atgtggaaag agagtactct attattcaag   13200
ttggaccaaa tcatcctcag gcaggatgga gtctgggagg aagggtgca ggggagaaca   13260 ggagagtgcc atggtggttt tgaaaatgct tatctcctat gtgtctccag aagggtagg   13320 gggggcttgg tgtaggatat cagaccccctt aggcagatgg aggacaggct tgtctgcagc   13380
acgctgacca cctcacttct actctcagcc aagggaggtc ccttctgact gattttttgg   13440
agagaaggaa ccagatagaa gaaactttag cctggtgaga atacagggtg tgaattgccc   13500
ccgccccccc cccccccaa tcagggctgc aggtgtgcta cactgggtac agaataaggg   13560
cctcccaggc ctccctcagc tctctccact tcttgactga gtccagggac ctctagccct   13620
ggcccttgca tgaagaaagg aaaagtgcac tgtcccttta agccccagc cagggccgcc   13680 tccagagccc catcccccctt caatttaatt tcattaaaac agagcatgaa tatttctatt   13740
aaacctaaaa tgaaatatga agccatttag actctgcctg caccaatcac ccagatttat   13800 gactttttatt catcacatca agagcttgga aaaatgaatt ttcttcaccc aggaaggaaa   13860
taaaacctca ggcttggtca tttccagaaa gctgttaatt tgaccatgtg gtaattactt   13920
tcacaattaa ctaaaataca aatcaacttg acaaattgag ctagtttata tattaattag   13980
cctgcttaaa tttattcatt atgaaaagac aatttaaggg gacctgcagt gtctgttttta   14040 ttgcaataaa ttattgtaag gaaatgggac caataagaca tcataatatt taaagatata   14100
gtacacgcgt ggggtgtgct ttattgacaa tttcatttttc caattagtaa ttttgttgta   14160
atatatctgc ggaccccaga ctcctggcca gggagacagg atcccccagg accagggagg   14220
tcagagtggc aggtcggagc ctcaggagtg aaggccaggt ccgttgagca gcaagtctgt   14280
tcccatgcaa gtcctggggt gcagcgagca aaaccaagtc cgcgcaacgg acccaggcag   14340
agatgcagtg cccagggget cctcctccct gcaggtcgag gggctgattt aatagaatgt   14400
cgatagaatc attcgatgcc ttttagcttg tgatctttat aaatgtccgt ctattaaatt   14460
acaaaatgat tctcttctcg tttaattgta ttctttcgtt tcttatttcc aattaattag   14520
tcctatcgac gttgcaatat attaagcgac tggagtccgt ttccagttag gatatatggg   14580
tcaacacatt ccgttttata ctcgacagaa ctatataatg tgggttttaa ctactcatcc   14640
ccatttgtct taaacacctg gccctcttga gtctccttcc tggcgtttgg tgggccccca   14700
tggcccctct tgagtctcct tcctggcgtt tggtgggccc ccatggcccc tctttgcttc   14760
cctgctcctg aatgcacagc tcagtctgaa aggctgccag agcctttgga attgtttgtt   14820
ttaaacgtgt ccatcttact ggattcggga caaacaggtc tgcagaagat actagtggtt   14880
caatatctga aggtttatat tccctcaaag cagggtgggt gggggaatg agactgctgg   14940 gcagtcagtg gtgccccctg tccctcgtg ccctctttgg ccctttcttt ccggagagcc   15000 tcccttttata accctaggta gttccaaaa ccggggctac atagctcaga cttgccttca   15060
atgttgtgct attcatttac ttctgccgtg gggttacaag tgtgtgccac cacttccact   15120
cataaaatta cctttaaata tacgggactt tagatttccc cctccttgat cttctcccct   15180
tgcctttgct gtggtgggac ggacatatgt                                    15210
```